(12) United States Patent
Soll et al.

(10) Patent No.: US 7,919,522 B2
(45) Date of Patent: Apr. 5, 2011

(54) COMPOSITIONS COMPRISING C-13 ALKOXYETHER MACROLIDE COMPOUNDS AND PHENYLPYRAZOLE COMPOUNDS

(75) Inventors: Mark D. Soll, Alpharetta, GA (US); Albert Boeckh, Cumming, GA (US); Natalya Shub, Bridgewater, NJ (US)

(73) Assignee: Merial Limited, Duluth, GA (US)

( * ) Notice: Subject to any disclaimer, the term of this patent is extended or adjusted under 35 U.S.C. 154(b) by 811 days.

(21) Appl. No.: 11/799,796

(22) Filed: May 3, 2007

(65) Prior Publication Data
US 2007/0293446 A1 Dec. 20, 2007

(51) Int. Cl.
*A61K 31/335* (2006.01)
*C07D 309/30* (2006.01)
(52) U.S. Cl. .......... 514/450; 549/292; 504/292
(58) Field of Classification Search .......... None
See application file for complete search history.

(56) References Cited

U.S. PATENT DOCUMENTS

| | | | | |
|---|---|---|---|---|
| 4,468,390 A | * | 8/1984 | Kitano | 514/161 |
| 6,127,364 A | * | 10/2000 | Dyker et al. | 514/229.2 |
| 6,136,838 A | * | 10/2000 | Chern et al. | 514/404 |

FOREIGN PATENT DOCUMENTS

| | | |
|---|---|---|
| EP | 0 184 173 A | 6/1986 |
| EP | 0357460 A2 | 3/1990 |
| EP | 0444964 A1 | 3/1991 |
| EP | 0 530 901 A | 3/1993 |
| EP | 0594291 A1 | 9/1993 |
| WO | WO 98/11780 A | 3/1998 |

OTHER PUBLICATIONS

Cvetovich R.J. ,et al.: "Practical Synthesis of 13-0-[(2-Methoxyethoxy)methyl]-22,23-dihydroavermectin B1 Aglycon [Dimedectin Isopropanol, MK-324] and13-epi-O-(Methoxymethyl)-22,23-dihyroavermectin B1 Aglycon [L-694,554], Flea Active Ivermectin Analogues" J. Org. Chem., vol. 62, 1997, pp. 3989-3993.

\* cited by examiner

*Primary Examiner* — Elli Peselev
(74) *Attorney, Agent, or Firm* — Judy Jarecki-Black; John Ezcurra; Merial Limited

(57) ABSTRACT

Provided is a novel ivermectin derivative and compositions for the treatment or prophylaxis of parasite infestations in mammals or birds which comprise:
(A) a pharmaceutically effective amount of a 1-N-phenylpyrazole compound;
(B) a pharmaceutically effective amount of an ivermectin derivative of formula (II)

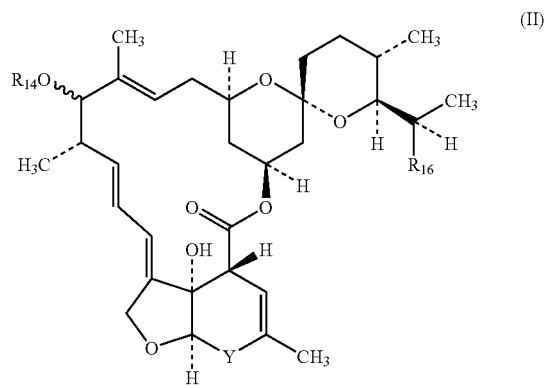

wherein:
$R_{14}$ represents $-(CH_2)_s-O-Z$
wherein,
s is 1 or 2;
Y represents $-CH(OR_{15})-$, $-C(=O)-$ or $-C(=NOR_{15})$;

$R_{15}$ represents hydrogen, alkyl or phenyl; and
$R_{16}$ represents —$CH_3$ or —$CH_2CH_3$;
Z is alkyl, alkenyl, alkynyl, acyl, alkylalkoxy, aryl, alkanoyloxy, alkoxycarbonyl, alkenoyl, alkynoyl, or aroyl.

24 Claims, 6 Drawing Sheets

COMPOSITIONS COMPRISING C-13 ALKOXYETHER MACROLIDE COMPOUNDS AND PHENYLPYRAZOLE COMPOUNDS

RELATED APPLICATIONS

This application makes reference to U.S. application Ser. No. 11/317,932, filed on Dec. 22, 2005 and U.S. application Ser. No. 10/279,356, filed Oct. 24, 2002, now allowed, which is a continuation-in-part of U.S. application Ser. No. 10/155, 397, filed May 24, 2002, now U.S. Pat. No. 6,962,713, which is a divisional of U.S. application Ser. No. 09/376,736, filed Aug. 17, 1999, now U.S. Pat. No. 6,426,333, which is a continuation-in-part of U.S. application Ser. No. 09/271,470, filed Mar. 17, 1999, now U.S. Pat. No. 6,482,425, which is a continuation-in-part of International application No. PCT/FR97/01548, filed Sep. 15, 1997, designating the U.S., and claiming priority to French application No. 96/11446, filed Sep. 19, 1996.

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

This invention relates to compositions comprising an N-phenylpyrazole and a novel ivermectin derivative for combating parasites in birds and mammals. This invention also provides for an improved method for eradicating, controlling, and preventing parasite infestation in birds and mammals. This invention also provides for novel ivermectin derivatives.

BACKGROUND OF THE INVENTION

Animals such as mammals and birds are often susceptible to parasite infestations. These parasites may be ectoparasites, such as insects, and endoparasites such as filariae and worms. Domesticated animal, such as cats and dogs, are often infested with one or more of the following ectoparasites:

cat and dog fleas (*Ctenocephalides felis, Ctenocephalides* sp. and the like),
ticks (*Rhipicephalus* sp., *Ixodes* sp., *Dermacentor* sp., *Amblyoma* sp. and the like), and
mites (*Demodex* sp., *Sarcoptes* sp., *Otodectes* sp. and the like),
lice (*Trichodectes* sp., *Cheyletiella* sp., *Lignonathus* sp., and the like),
mosquitoes (*Aedes* sp., *Culex* sp., *Anopheles* sp., and the like) and
flies (*Hematobia* sp., *Musca* sp., *Stomoxys* sp., *Dermatobia* sp., *Coclyomia* sp., and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and humans.

Similarly, ticks are also harmful to the physical and psychological health of the animal or human. However, the most serious problem associated with ticks is that they are the vector of pathogenic agents, agents which cause diseases in both humans and animal. Major diseases which are caused by ticks include borrelioses (Lyme disease caused by *Borrelia burgdorferi*), babesioses (or piroplasmoses caused by *Babesia* sp.) and rickettsioses (also known as Rocky Mountain spotted fever). Ticks also release toxins which cause inflammation or paralysis in the host. Occasionally, these toxins are fatal to the host.

Moreover, mites and lice are particularly difficult to combat since there are very few active substances which act on these parasites and they require frequent treatment.

Likewise, farm animals are also susceptible to parasite infestations. For example, cattle are affected by a large number of parasites. A parasite which is very prevalent among farm animals is a tick genus *Boophilus*, especially those of the species microplus (cattle tick), decoloratus and anulatus. Ticks, such as *Boophilus* microplus, are particularly difficult to control because they live in the pasture where the farm animals graze. Other important parasites of cattle and sheep are listed as follows in order of decreasing importance:

myiases such as *Dermatobia hominis* (known as Berne in Brazil) and *Cochlyomia hominivorax* (greenbottle); sheep myiases such as *Lucilia sericata, Lucilia cuprina* (known as blowfly strike in Australia, New Zealand and South Africa). These are flies whose larva constitutes the animal parasite;

flies proper, namely those whose adult constitutes the parasite, such as *Haematobia irritans* (horn fly);

lice such as *Linognathus vitulorum*, etc.; and mites such as *Sarcoptes scabiei* and *Psoroptes ovis*.

The above list is not exhaustive and other ectoparasites are well known in the art to be harmful to animals and humans. These include, for example migrating dipterous larvae.

Animals and humans also suffer from endoparasitical infections including, for example, helminthiasis which is most frequently caused by a group of parasitic worms described as nematodes or roundworms. These parasites cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichiris, Enterobius* and parasites which are found in the blood or other tissues and organs such as filarial worms and the extra intestinal stages of Strogyloides, Toxocara and *Trichinella*.

Many insecticides exist in the art for treating parasites. These insecticides vary in their effectiveness to a particular parasite as well as their cost. However the results of these insecticides is not always satisfactory because of, for example, the development of resistance by the parasite to the therapeutic agent, as is the case, for example, with carbamates, organophosphorus compounds and pyrethroids. Moreover, there is at the present time no truly effective method for controlling both ticks and helminths and less still an effective way of controlling the set of parasites indicated above. Thus, there is a need in the art for more effective antiparasitic formulation treatment and protection of animal, e.g. mammals, fish and birds for a wide range of parasites. Moreover, there is a need in the art for antiparasitic formulation which is easy to use on any type of domestic animal, irrespective of its size and the nature of its coat and which do not need to be sprinkled over the entire body of the mammal, fish or bird.

A new family of insecticides based on 1-N-phenylpyrazoles is described in Patents EP-A-295,217 and EP-A-352, 944. The compounds of the families defined in these patents are extremely active and one of these compounds, 1-[2,6-$Cl_2$-4-$CF_3$ phenyl]-3-CN-4-[SO-$CF_3$]-5-$NH_2$ pyrazole, or fipronil, is particularly effective, not only against crop parasites but also against ectoparasites of mammals and birds. Fipronil is particularly, but not exclusively, effective against fleas and ticks.

Endectocidal compounds, which exhibit a degree of activity against a wide range endoparasites, are known in the art. These compounds possess a macrocyclic lactone ring and are known in the art to be particularly effective against ectoparasites, including lice, blowflies, flies, mosquitoes, mites, migrating dipterous larvae, and ticks, as well as endoparasites, such as nematodes and roundworms. Compounds of this group include avermectins, milbemycins, and derivatives of these compounds, for example, ivermectin or emamectin. Such substances are described, for example, in U.S. Pat. Nos. 3,950,360; 4,199,569; 4,879,749; and 5,268,710.

While it is known in the art that it is sometimes possible to combine various parasiticides in order to broaden the antiparasitical spectrum, it is not possible to predict, a priori, which combinations will work for a particular animal or disease state. For this reason, the results of various combinations is not always successful and there is a need in the art for more effective formulations which may be easily administered to the animal. The effectiveness of formulations comprising 1-N-phenylpyrazole derivatives and macrolide lactone anthelmintic or parasitic agents, such as avermectins, ivermectins and milbemycin, against an endoparasite or an ectoparasite in a specific host is especially difficult to predict because of the numerous and complex host-parasite interactions.

Patent application AU-A-16 427/95 very broadly mentions the combination of a substituted 1-N-pyrazole derivatives with an avermectin, ivermectin or moxidectin in a discussion involving among a very large number of insecticides or parasiticides of various types, including fipronil. However, this patent application does not provide specific guidance to the skilled artisan on how to formulate a 1-N-pyrazole derivative with an avermectin or milbemycin type compound, let alone how to formulate a spot-on composition comprising these compounds. Moreover, the application does not indicate which specific parasites are susceptible to what specific combination.

Various methods of formulating antiparasitical formulations are known in the art. These include oral formulations, baits, dietary supplements, powders, shampoos, pastes, concentrated solution, suspension, microemulsion, emulsion etc. Formulations for localized topical applications of antiparasitical formulations are also known in the art.

Ready-to-use solutions comprising 1-N-phenylpyrazoles, such as fipronil, are known in the art and are described in U.S. Pat. No. 6,395,765, herein incorporated by reference.

Pour-on solutions comprising 1-N-phenylpyrazoles, such as fipronil, are known in the art and are described in U.S. Pat. No. 6,010,710, herein incorporated by reference.

Spot-on formulations are well known techniques for topically delivering an antiparasitic agent to a limited area of the host. Spot-on formulations comprising a 1-N-phenylpyrazole and a macrocyclic lactone are described in U.S. Pat. No. 6,426,333.

Paste formulations are also an effective means of delivering an antiparasitic agent to an area on the host. Paste formulations are described in U.S. Pat. No. 6,787,342.

While compositions containing 1-N-phenylpyrazole and a macrocyclic lactone are generally known in the art, the ivermectin derivatives described for use herein are novel compounds. In addition, it would be beneficial if compositions for combating parasites could have fast acting and long lasting effects in order to reduce the number of applications necessary to combat parasites. Moreover, it is well known that parasites have a tendency to develop resistance against known therapeutic agents and it would be beneficial to develop novel compositions to combat parasites.

For the purposes of this application, unless otherwise stated in the specification, the following terms have the definitions cited below:

(1) Alkyl refers to both straight and branched carbon chains; references to individual alkyl groups are specific for the straight chain (e.g. butyl=n-butyl). In one embodiment of alkyl, the number of carbons atoms is 1-20, in another embodiment of alkyl, the number of carbon atoms is 1-8 carbon atoms and in yet another embodiment of alkyl, the number of carbon atoms is 1-4 carbon atoms. Other ranges of carbon numbers are also contemplated depending on the location of the alkyl moiety on the molecule;

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in another embodiment of alkenyl, the number of carbon atoms is 2-8 and in yet another embodiment of alkenyl, the number of carbon atoms is 2-4. Other ranges of carbon-carbon double bonds and carbon numbers are also contemplated depending on the location of the alkenyl moiety on the molecule;

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in another embodiment of alkynyl, the number of carbon atoms is 2-8 and in yet another embodiment of alkynyl, the number of carbon atoms is 2-4. Other ranges of carbon-carbon double bonds and carbon numbers are also contemplated depending on the location of the alkenyl moiety on the molecule;

(4) Aryl refers to a $C_6$-$C_{10}$ aromatic ring structure. In one embodiment of aryl, the moiety is phenyl, naphthyl, tetrahydronapthyl, phenylcyclopropyl and indanyl; in another embodiment of aryl, the moiety is phenyl.

(5) Alkoxy refers to —O-alkyl, wherein alkyl is as defined in (1); Alkylalkoxy refers to -alkyl-O-alkyl, wherein alkyl is as defined in (1);

(6) Alkanoyl or acyl refers to formyl (—C(=O)H) and —C(=O)-alkyl, wherein alkyl is as defined in (1);

(7) Alkanoyloxy refers to —O—C(=O)-alkyl, wherein alkanoyl is as defined in (6);

(8) Alkanoylamino refers to —NH$_2$—C(=O)-alkyl, wherein alkanoyl is as defined in (6) and the amino (NH$_2$) moiety can be substituted by alkyl as defined in (1);

(9) Aminocarbonyl refers to —NH$_2$—C(=O), wherein the amino (NH$_2$) moiety can be substituted by alkyl as defined in (1);

(10) Alkoxycarbonyl refers to —C(=O)—O-alkyl, wherein alkoxy is as defined in (5);

(11) Alkenoyl refers to —C(=O)-alkenyl, wherein alkenyl is as defined in (2);

(12) Alkynoyl refers to —C(=O)-alkynyl, wherein alkynyl is as defined in (3);

(13) Aroyl refers to —C(=O)-aryl, wherein aryl is as defined above;

(14) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo- moiety on the molecule;

(15) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$));

(16) Heterocycle, heterocyclic or heterocyclo refer to fully saturated or unsaturated, including aromatic (i.e. "heteroaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl]or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means a C-13 alkoxyether macrolide compound or phenylpyrazole compound of the invention It is also noted that this disclosure and in the claims and/or paragraphs, the C-13 alkoxyether macrolide compounds of the invention and the term "phenylpyrazole compound" as used to describe the invention is intended to include all stereoisomers and crystalline forms (which includes hydrated forms, polymorphic forms and amorphous forms with up to 15% by weight crystalline structure) thereof.

It is noted that in this disclosure and in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

SUMMARY OF THE INVENTION

The invention provides for compositions for the treatment or prophylaxis of parasites of mammals and birds, and in particular, cats, dogs, horses, chickens, sheep and cattle with the aim of ridding these hosts of all the parasites commonly encountered by mammals and birds. The invention also provides for effective and long lasting destruction of ectoparasites, such as fleas, ticks, mites, e.g. itch mites, mosquitoes, flies and lice, and of endoparasites, nematodes, such as filariae, hookworms, whipworms and roundworms of the digestive tract of animals and humans.

In particular this invention provides for novel composition for the treatment or prophylaxis of parasite infestations in mammals or birds which comprise:
(A) an effective amount of a 1-N-phenylpyrazole derivative;
(B) an effective amount of an ivermectin derivative; and
(C) a pharmaceutically effective carrier.

The invention also provides for an easy method of treating parasitic infestations or for the prophylaxis of parasite infestations in mammals or birds which comprises topically applying to said mammal or bird an effective amount of a formulation according to the present invention.

This invention also provides for compositions comprising a combination of a 1-N-phenylpyrazole derivative and an ivermectin derivative which exhibit synergistic activity against parasites when compared to formulations which contain only one class of therapeutic agent.

This invention also provides a novel ivermectin derivative compound, the method of making said compound and compositions comprising the compound.

The very high effectiveness of the method and of the composition/formulations according to the invention provides not only for a high instantaneous effectiveness but also for an effectiveness of very long duration after the treatment of the mammal or bird. The compositions/formulations also provide an alternative to other commercial antiparasitic formulations such as FRONTLINE® (fipronil) and K-9 ADVANTIX(® (imidacloprid/permethrin) should a parasite develop a resistance to these formulations.

For the purpose of this invention the term "pharmaceutical"/"pharmaceutically" is intended to encompass treatment of animals, humans and birds.

These and other embodiments are disclosed or are obvious from and encompassed by the following Detailed Description. As will be apparent, preferred features and characteristics of one aspect of the invention are applicable to many other aspects of the invention.

In this disclosure, "comprises," "comprising," "containing" and "having" and the like can have the meaning ascribed to them in U.S. Patent law and can mean "includes," "including," and the like; "consisting essentially of" or "consists essentially of" likewise has the meaning ascribed in U.S. Patent law and the term is open-ended, allowing for the presence of more than that which is recited, so long as basic or novel characteristics of that which is recited are not changed by the presence of more than that which is recited, but excludes prior-art embodiments.

BRIEF DESCRIPTION OF THE DRAWINGS

Various preferred features and embodiments of the present invention will now be described in more detail by way of non-limiting example and with reference to the accompanying Figures, in which.

DETAILED DESCRIPTION

Figure 1:
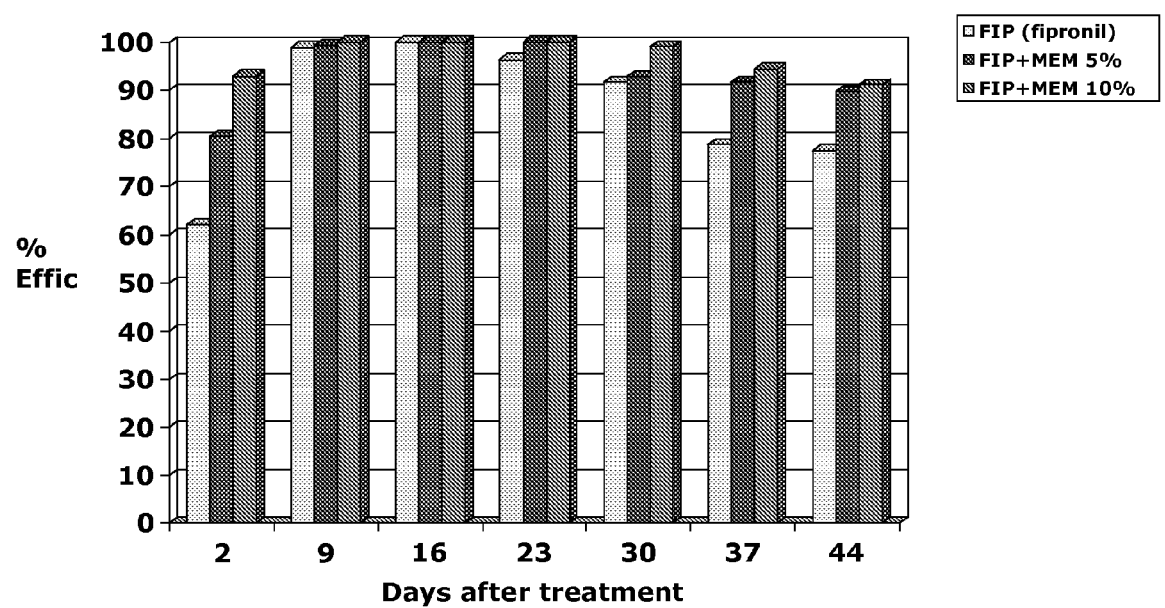
FIG. 1 compares the efficacy against ticks in dogs after administering a fipronil containing composition vs. a fipronil and ivermectin derivative containing composition.

This invention provides for a composition for the treatment or prophylaxis of parasite infestation in birds or mammals which comprises:
(A) a pharmaceutically effective amount of at least one compound of the formula (I)

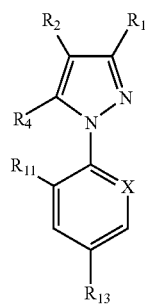

wherein:
$R_1$ is a halogen, CN or alkyl;
$R_2$ is $S(O)_n R_3$, 4,5-dicyanoimidazol-2-yl or haloalkyl;
$R_3$ is alkyl or haloalkyl;
$R_4$ represents a hydrogen, halogen, $NR_5R_6$, $S(O)_m R_7$, $C(O)R_7$, $C(O)OR_7$, alkyl, haloalkyl, $OR_8$ radical or —N=C($R_9$)($R_{10}$) radical;
$R_5$ and $R_6$ independently represent hydrogen, alkyl, haloalkyl, C(O)alkyl, $S(O)_r CF_3$, alkoxycarbonyl; or
$R_5$ and $R_6$ can together form a divalent alkylene radical which is optionally interrupted by one or two divalent heteroatoms;
$R_7$ represents an alkyl or haloalkyl;
$R_8$ represents an alkyl, haloalkyl or hydrogen;
$R_9$ represents an alkyl or hydrogen;
$R_{10}$ represents an optionally substituted aryl or an optionally substituted heteroaryl group;
$R_{11}$ and $R_{12}$ represent, independently of one another, hydrogen, halogen, CN or $NO_2$;
$R_{13}$ represents a halogen, haloalkyl, haloalkoxy, $S(O)_q CF_3$ or $SF_5$;
m, n, q and r represent, independently of one another, an integer equal to 0, 1 or 2;
X represents a trivalent nitrogen atom or a C—$R_{12}$ radical, the three other valencies of the carbon atom forming part of the aromatic ring;
(B) a pharmaceutically effective amount of an ivermectin derivative of the formula (II):

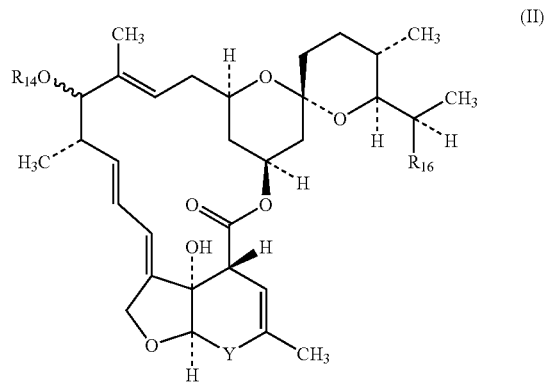

wherein:
$R_{14}$ represents —$(CH_2)_s$—O—Z
wherein,
s is 1 or 2;
Y represents —$CH(OR_{15})$—, —$C(=O)$— or —$C(=NOR_{15})$;
$R_{15}$ represents hydrogen, alkyl or phenyl; and
$R_{16}$ represents —$CH_3$ or —$CH_2CH_3$;
Z is alkyl, alkenyl, alkynyl, acyl, alkylalkoxy, aryl, alkanoyloxy, alkoxycarbonyl, alkenoyl, alkynoyl, or aroyl
(C) a pharmaceutically acceptable carrier.

In another embodiment of the invention for the compound of formula (II), the composition for the treatment or prophylaxis of parasite infestation in birds or mammals comprises:
(A) a pharmaceutically effective amount of at least one compound of the formula (I)

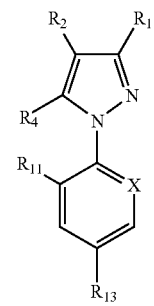

wherein:
$R_1$ is a halogen, CN or $C_1$-$C_8$ alkyl;

$R_2$ is $S(O)_nR_3$ or $C_1$-$C_8$ haloalkyl;

$R_3$ is $C_1$-$C_8$ alkyl or $C_1$-$C_8$ haloalkyl;

$R_4$ represents a hydrogen, halogen, $NR_5R_6$, $S(O)_mR_7$, $C(O)R_7$, $C(O)OR_7$, $C_1$-$C_8$ alkyl, $C_1$-$C_8$ haloalkyl, $OR_8$ radical;

$R_5$ and $R_6$ independently represent hydrogen, $C_1$-$C_8$ alkyl, $C(O)$alkyl; or $R_7$ represents an $C_1$-$C_8$ alkyl or $C_1$-$C_8$ haloalkyl;

$R_8$ represents an $C_1$-$C_8$ alkyl, $C_1$-$C_8$ haloalkyl or hydrogen;

$R_{11}$ and $R_{12}$ represent, independently of one another, hydrogen, halogen, CN or $NO_2$;

$R_{13}$ represents a halogen, $C_1$-$C_8$ haloalkyl, $C_1$-$C_8$ haloalkoxy, $S(O)_qCF_3$ or $SF_5$;

m, n, q and r represent, independently of one another, an integer equal to 0, 1 or 2;

X represents a trivalent nitrogen atom or a C—$R_{12}$ radical, the three other valencies of the carbon atom forming part of the aromatic ring;

(B) a pharmaceutically effective amount of an ivermectin derivative of the formula (II):

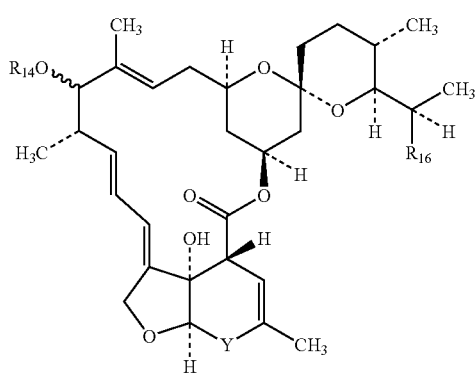

(II)

wherein:

$R_{14}$ represents —$(CH_2)_s$—O—Z
  wherein,
  s is 1 or 2;

Y represents —$CH(OR_{15})$—, —$C(=O)$— or —$C(=NOR_{15})$;

$R_{15}$ represents hydrogen, or $C_1$-$C_8$ alkyl; and $R_{16}$ represents —$CH_3$ or —$CH_2CH_3$;

Z is $C_1$-$C_8$ alkyl, $C_1$-$C_8$ acyl, or $C_1$-$C_8$ alkylalkoxy, (C) a pharmaceutically acceptable carrier.

In another embodiment of the invention for the compound of formula (II), the composition for the treatment or prophylaxis of parasite infestation in birds or mammals comprises:

(A) a pharmaceutically effective amount of at least one compound of the formula (I)

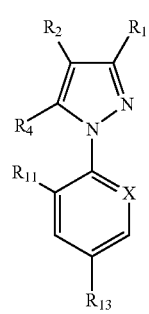

(I)

wherein:
$R_1$ is a halogen, CN or $C_1$-$C_4$ alkyl;
$R_2$ is $S(O)_nR_3$ or $C_1$-$C_4$ haloalkyl;
$R_3$ is $C_1$-$C_4$ alkyl or $C_1$-$C_4$ haloalkyl;
$R_4$ represents a hydrogen, fluorine, chlorine, bromine, $NR_5R_6$, $S(O)_mR_7$, $C(O)R_7$, $C(O)OR_7$, $C_1$-$C_4$ alkyl, $C_1$-$C_4$ haloalkyl, $OR_8$ radical;
$R_5$ and $R_6$ independently represent hydrogen, $C_1$-$C_4$ alkyl, $C(O)$alkyl; or
$R_7$ represents an $C_1$-$C_4$ alkyl or $C_1$-$C_4$ haloalkyl;
$R_8$ represents an $C_1$-$C_4$ alkyl, $C_1$-$C_4$ haloalkyl or hydrogen;
$R_{11}$ and $R_{12}$ represent, independently of one another, hydrogen, halogen, CN or $NO_2$;
$R_{13}$ represents a halogen, $C_1$-$C_4$ haloalkyl, $C_1$-$C_4$ haloalkoxy, $S(O)_qCF_3$ or $SF_5$;
m, n, q and r represent, independently of one another, an integer equal to 0, 1 or 2;
X represents a trivalent nitrogen atom or a C—$R_{12}$ radical, the three other valencies of the carbon atom forming part of the aromatic ring;

(B) a pharmaceutically effective amount of an ivermectin derivative of the formula (II):

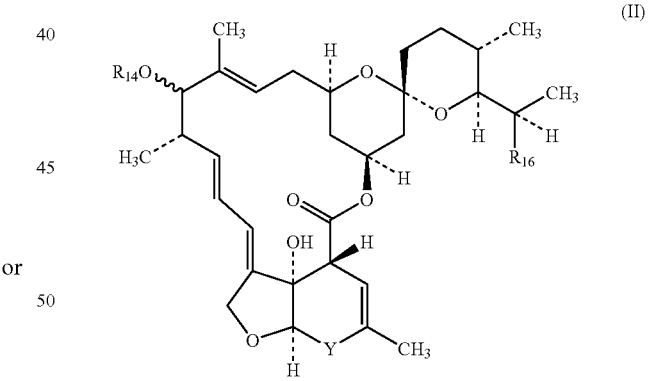

(II)

wherein:
$R_{14}$ represents —$(CH_2)_s$—O—Z
  wherein,
  s is 1;
Y represents —$CH(OR_{15})$—, —$C(=O)$— or —$C(=NOR_{15})$;
$R_{15}$ represents hydrogen, or $C_1$-$C_8$ alkyl; and
$R_{16}$ represents —$CH_3$ or —$CH_2CH_3$;
Z is $C_1$-$C_4$ alkyl, $C_1$-$C_4$ acyl, or $C_1$-$C_4$ alkylalkoxy,
(C) a pharmaceutically acceptable carrier.

In an embodiment of the invention for formula (II), the composition for the treatment and prophylaxis of parasite infestation in birds or mammals comprises:

(A) a pharmaceutically effective amount of at least one compound of the formula (I)

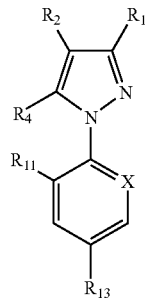

(I)

wherein:
$R_1$ is CN;
$R_2$ is $S(O)_nR_3$;
$R_3$ is $CF_3$;
$R_4$ represents $NR_5R_6$;
$R_5$ and $R_6$ independently represent hydrogen;
$R_{11}$ and $R_{12}$ represent Cl;
$R_{13}$ represents $CF_3$;
n is 1;
X represents C—$R_{12}$
(this compound is also known as fipronil); and
(B) a pharmaceutically effective amount of an ivermectin derivative of the formula (II):

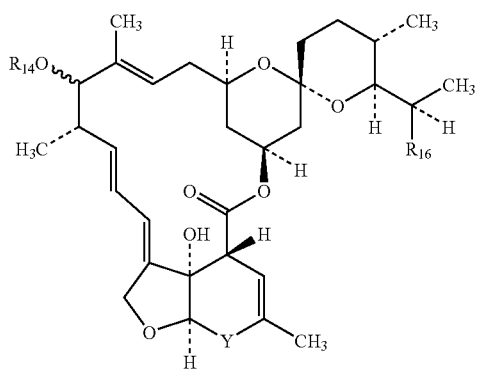

(II)

wherein:
$R_{14}$ represents —$(CH_2)_s$—O—Z
  wherein,
  s is 1;
Y represents —$CH(OR_{15})$—, —C(=O)— or —$C(=NOR_{15})$;
$R_{15}$ represents hydrogen, or $C_1$-$C_8$ alkyl; and
$R_{16}$ represents —$CH_3$ or —$CH_2CH_3$;
Z is $C_1$-$C_4$ alkyl, $C_1$-$C_4$ acyl, or $C_1$-$C_4$ alkylalkoxy,
(C) a pharmaceutically acceptable carrier.

In another embodiment of the invention for formula (IIa), the composition for the treatment or prophylaxis of parasite infestation in birds or mammals comprises:
(A) a pharmaceutically effective amount of at least one compound of the formula (I)

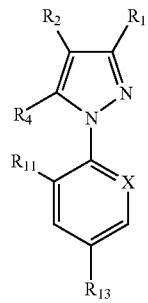

(I)

wherein:
$R_1$ is a halogen, CN or alkyl;
$R_2$ is $S(O)_nR_3$, 4,5-dicyanoimidazol-2-yl or haloalkyl;
$R_3$ is alkyl or haloalkyl;
$R_4$ represents a hydrogen, halogen, $NR_5R_6$, $S(O)_mR_7$, $C(O)R_7$, $C(O)OR_7$, alkyl, haloalkyl, $OR_8$ radical or —N=$CR_9)R_{10}$) radical;
$R_5$ and $R_6$ independently represent hydrogen, alkyl, haloalkyl, C(O)alkyl, $S(O)_rCF_3$, alkoxycarbonyl; or
$R_5$ and $R_6$ can together form a divalent alkylene radical which is optionally interrupted by one or two divalent heteroatoms;
$R_7$ represents an alkyl or haloalkyl;
$R_8$ represents an alkyl, haloalkyl or hydrogen;
$R_9$ represents an alkyl or hydrogen;
$R_{10}$ represents an optionally substituted aryl or an optionally substituted heteroaryl group;
$R_{11}$ and $R_{12}$ represent, independently of one another, hydrogen, halogen, CN or $NO_2$;
$R_{13}$ represents a halogen, haloalkyl, haloalkoxy, $S(O)_qCF_3$ or $SF_5$; m, n, q and r represent, independently of one another, an integer equal to 0, 1 or 2;
X represents a trivalent nitrogen atom or a C—$R_{12}$ radical, the three other valencies of the carbon atom forming part of the aromatic ring;
(B) a pharmaceutically effective amount of an ivermectin derivative of the formula (IIa):

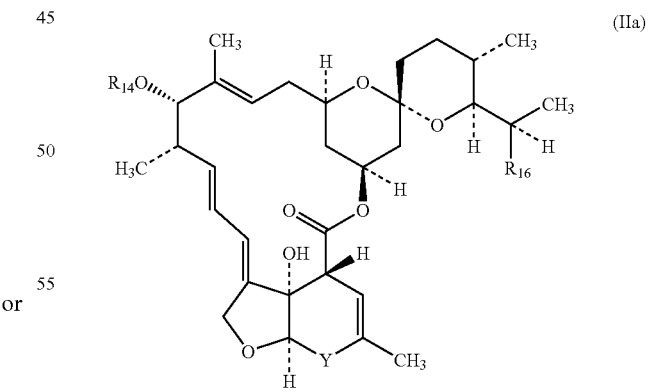

(IIa)

wherein:
$R_{14}$ represents —$(CH_2)_s$—O—Z
  wherein,
  s is 1 or 2;
Y represents —$CH(OR_{15})$—, —C(=O)— or —$C(=NOR_{15})$;
$R_{15}$ represents hydrogen, $C_1$-$C_4$ alkyl or phenyl; and $R_{16}$ represents —CH$_3$ or —CH$_2$CH$_3$;

Z is alkyl, alkenyl, alkynyl, acyl, alkylalkoxy, aryl, alkanoyloxy, alkoxycarbonyl, alkenoyl, alkynoyl, or aroyl; and (C) a pharmaceutically acceptable carrier.

In another embodiment of the invention for the compound of formula (IIa), the composition for the treatment or prophylaxis of parasite infestation in birds or mammals comprises:

(A) a pharmaceutically effective amount of at least one compound of the formula (I)

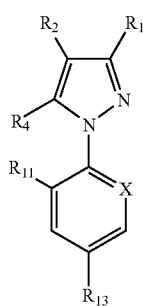

(I)

wherein:
$R_1$ is a halogen, CN or C$_1$-C$_8$ alkyl;
$R_2$ is S(O)$_n$R$_3$ or C$_1$-C$_8$ haloalkyl;
$R_3$ is C$_1$-C$_8$ alkyl or C$_1$-C$_8$ haloalkyl;
$R_4$ represents a hydrogen, halogen, NR$_5$R$_6$, S(O)$_m$R$_7$, C(O)R$_7$, C(O)OR$_7$, C$_1$-C$_8$ alkyl, C$_1$-C$_8$ haloalkyl, OR$_8$ radical;
$R_5$ and $R_6$ independently represent hydrogen, C$_1$-C$_8$ alkyl, C(O)alkyl; or
$R_7$ represents an C$_1$-C$_8$ alkyl or C$_1$-C$_8$ haloalkyl;
$R_8$ represents an C$_1$-C$_8$ alkyl, C$_1$-C$_8$ haloalkyl or hydrogen;
$R_{11}$ and $R_{12}$ represent, independently of one another, hydrogen, halogen, CN or NO$_2$;
$R_{13}$ represents a halogen, C$_1$-C$_8$ haloalkyl, C$_1$-C$_8$ haloalkoxy, S(O)$_q$CF$_3$ or SF$_5$;
m, n, q and r represent, independently of one another, an integer equal to 0, 1 or 2;
X represents a trivalent nitrogen atom or a C—R$_{12}$ radical, the three other valencies of the carbon atom forming part of the aromatic ring;

(B) a pharmaceutically effective amount of an ivermectin derivative of the formula (IIa):

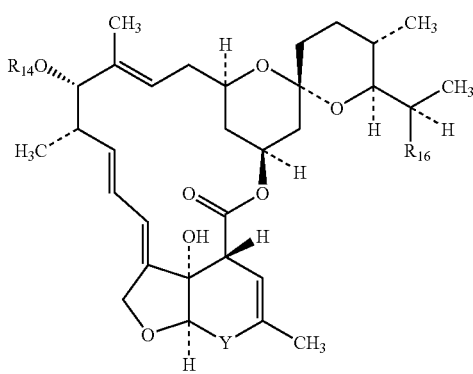

(IIa)

wherein:
$R_{14}$ represents —(CH$_2$)$_s$—O—Z wherein,
s is 1 or 2;
Y represents —CH(OR$_{15}$)—, —C(=O)— or —C(=NOR$_{15}$);
$R_{15}$ represents hydrogen, or C$_1$-C$_8$ alkyl; and
$R_{16}$ represents —CH$_3$ or —CH$_2$CH$_3$;
Z is C$_1$-C$_8$ alkyl, C$_1$-C$_8$ acyl, or C$_1$-C$_8$ alkylalkoxy, (C) a pharmaceutically acceptable carrier.

In another embodiment of the invention for the compound of formula (IIa), the composition for the treatment or prophylaxis of parasite infestation in birds or mammals comprises:

(A) a pharmaceutically effective amount of at least one compound of the formula (I)

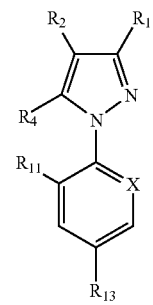

(I)

wherein:
$R_1$ is a halogen, CN or C$_1$-C$_4$ alkyl;
$R_2$ is S(O)$_n$R$_3$ or C$_1$-C$_4$ haloalkyl;
$R_3$ is C$_1$-C$_4$ alkyl or C$_1$-C$_4$ haloalkyl;
$R_4$ represents a hydrogen, fluorine, chlorine, bromine, NR$_5$R$_6$, S(O)$_m$R$_7$, C(O)R$_7$, C(O)OR$_7$, C$_1$-C$_4$ alkyl, C$_1$-C$_4$ haloalkyl, OR$_8$ radical;
$R_5$ and $R_6$ independently represent hydrogen, C$_1$-C$_4$ alkyl, C(O)alkyl; or
$R_7$ represents an C$_1$-C$_4$ alkyl or C$_1$-C$_4$ haloalkyl;
$R_8$ represents an C$_1$-C$_4$ alkyl, C$_1$-C$_4$ haloalkyl or hydrogen;
$R_{11}$ and $R_{12}$ represent, independently of one another, hydrogen, halogen, CN or NO$_2$;
$R_{13}$ represents a halogen, C$_1$-C$_4$ haloalkyl, C$_1$-C$_4$ haloalkoxy, S(O)$_q$CF$_3$ or SF$_5$;
m, n, q and r represent, independently of one another, an integer equal to 0, 1 or 2;
X represents a trivalent nitrogen atom or a C—R$_{12}$ radical, the three other valencies of the carbon atom forming part of the aromatic ring;

(B) a pharmaceutically effective amount of an ivermectin derivative of the formula (IIa):

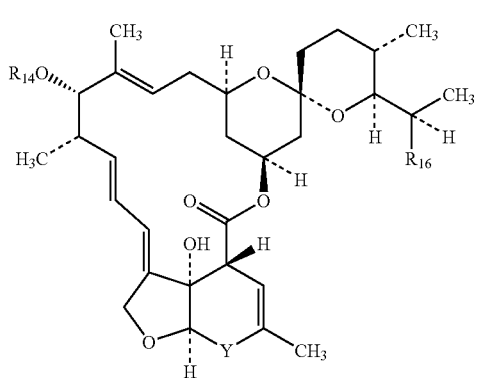

(IIa)

wherein:
$R_{14}$ represents —$(CH_2)_s$—O—Z
  wherein,
  s is 1;
Y represents —$CH(OR_{15})$—, —$C(=O)$— or —$C(=NOR_{15})$;
$R_{15}$ represents hydrogen, or $C_1$-$C_8$ alkyl; and
$R_{16}$ represents —$CH_3$ or —$CH_2CH_3$;
Z is $C_1$-$C_4$ alkyl, $C_1$-$C_4$ acyl, or $C_1$-$C_4$ alkylalkoxy,
(C) a pharmaceutically acceptable carrier.

In an embodiment of the invention for formula (IIa), the composition for the treatment and prophylaxis of parasite infestation in birds or mammals comprises:
(A) a pharmaceutically effective amount of at least one compound of the formula (I)

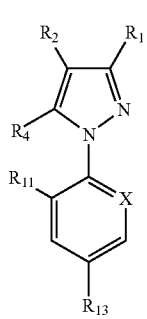

(I)

wherein:
$R_1$ is CN;
$R_2$ is $S(O)_n R_3$;
$R_3$ is $CF_3$;
$R_4$ represents $NR_5 R_6$;
$R_5$ and $R_6$ independently represent hydrogen;
$R_{11}$ and $R_{12}$ represent Cl;
$R_{13}$ represents $CF_3$;
n is 1;
X represents C—$R_{12}$
(this compound is also known as fipronil); and
(B) a pharmaceutically effective amount of an ivermectin derivative of the formula (IIa):

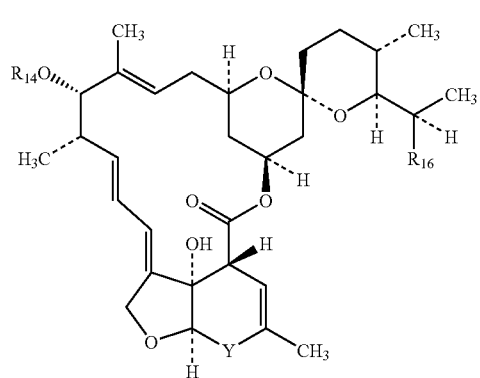

(IIa)

wherein:
$R_{14}$ represents —$(CH_2)_s$—O—Z
  wherein,
  s is 1;
Y represents —$CH(OR_{15})$—, —$C(=O)$— or —$C(=NOR_{15})$;
$R_{15}$ represents hydrogen, or $C_1$-$C_8$ alkyl; and
$R_{16}$ represents —$CH_3$ or —$CH_2CH_3$;
Z is $C_1$-$C_4$ alkyl, $C_1$-$C_4$ acyl, or $C_1$-$C_4$ alkylalkoxy,
(C) a pharmaceutically acceptable carrier.

In an embodiment of the invention for formula (IIa), the composition for the treatment and prophylaxis of parasite infestation in birds or mammals comprises:
(A) a pharmaceutically effective amount of at least one compound of the formula (I)

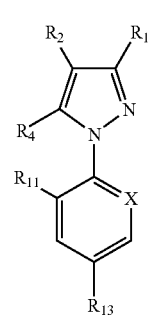

(I)

wherein:
$R_1$ is CN;
$R_2$ is $S(O)_n R_3$;
$R_3$ is $CF_3$;
$R_4$ represents $NR_5 R_6$;
$R_5$ and $R_6$ independently represent hydrogen;
$R_{11}$ and $R_{12}$ represent Cl;
$R_{13}$ represents $CF_3$;
n is 1;
X represents C—$R_{12}$
(this compound is also known as fipronil); and
(B) a pharmaceutically effective amount of an ivermectin derivative of the formula (III):

(III)

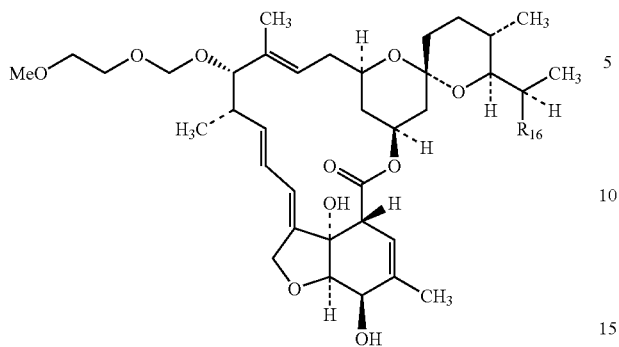

wherein:
$R_{16}$ represents —CH$_3$ or —CH$_2$CH$_3$; and
(C) a pharmaceutically acceptable carrier.

In another embodiment of the invention for formula (IIb), the composition for the treatment or prophylaxis of parasite infestation in birds or mammals comprises:
(A) a pharmaceutically effective amount of at least one compound of the formula (I)

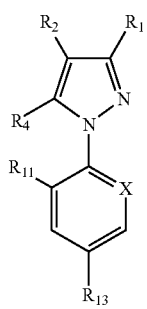

(I)

wherein:
$R_1$ is a halogen, CN or alkyl;
$R_2$ is S(O)$_n$R$_3$, 4,5-dicyanoimidazol-2-yl or haloalkyl;
$R_3$ is alkyl or haloalkyl;
$R_4$ represents a hydrogen, halogen, NR$_5$R$_6$, S(O)$_m$R$_7$, C(O)R$_7$, C(O)OR$_7$, alkyl, haloalkyl, OR$_8$ radical or —N=C(R$_9$)(R$_{10}$) radical;
$R_5$ and $R_6$ independently represent hydrogen, alkyl, haloalkyl, C(O)alkyl, S(O)$_r$CF$_3$, alkoxycarbonyl; or
$R_5$ and $R_6$ can together form a divalent alkylene radical which is optionally interrupted by one or two divalent heteroatoms;
$R_7$ represents an alkyl or haloalkyl;
$R_8$ represents an alkyl, haloalkyl or hydrogen;
$R_9$ represents an alkyl or hydrogen;
$R_{10}$ represents an optionally substituted aryl or an optionally substituted heteroaryl group;
$R_{11}$ and $R_{12}$ represent, independently of one another, hydrogen, halogen, CN or NO$_2$;
$R_{13}$ represents a halogen, haloalkyl, haloalkoxy, S(O)$_q$CF$_3$ or SF$_5$;
m, n, q and r represent, independently of one another, an integer equal to 0, 1 or 2;
X represents a trivalent nitrogen atom or a C—R$_{12}$ radical, the three other valencies of the carbon atom forming part of the aromatic ring;

(B) a pharmaceutically effective amount of an ivermectin derivative of the formula (IIb):

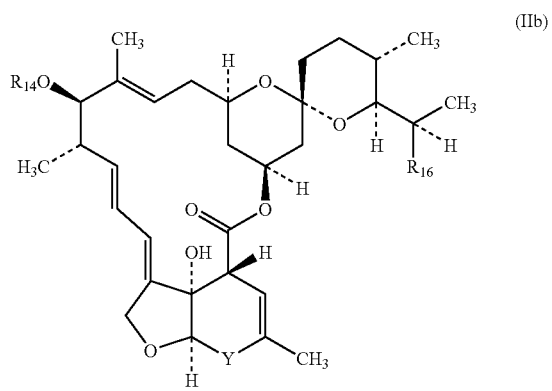

(IIb)

wherein:
$R_{14}$ represents —(CH$_2$)$_s$—O—Z
wherein,
s is 1 or 2;
Y represents —CH(OR$_{15}$)—, —C(=O)— or —C(=NOR$_{15}$);
$R_{15}$ represents hydrogen, C$_1$-C$_4$ alkyl or phenyl; and
$R_{16}$ represents —CH$_3$ or —CH$_2$CH$_3$;
Z is alkyl, alkenyl, alkynyl, acyl, alkylalkoxy, aryl, alkanoyloxy, alkoxycarbonyl, alkenoyl, alkynoyl, or aroyl; and
(C) a pharmaceutically acceptable carrier.

In another embodiment of the invention for the compound of formula (IIb), the composition for the treatment or prophylaxis of parasite infestation in birds or mammals comprises:
(A) a pharmaceutically effective amount of at least one compound of the formula (I)

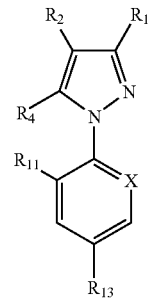

(I)

wherein:
$R_1$ is a halogen, CN or C$_1$-C$_8$ alkyl;
$R_2$ is S(O)$_n$R$_3$ or C$_1$-C$_8$ haloalkyl;
$R_3$ is C$_1$-C$_8$ alkyl or C$_1$-C$_8$ haloalkyl;
$R_4$ represents a hydrogen, halogen, NR$_5$R$_6$, S(O)$_m$R$_7$, C(O)R$_7$, C(O)OR$_7$, C$_1$-C$_8$ alkyl, C$_1$-C$_8$ haloalkyl, OR$_8$ radical;
$R_5$ and $R_6$ independently represent hydrogen, C$_1$-C$_8$ alkyl, C(O)alkyl; or
$R_7$ represents an C$_1$-C$_8$ alkyl or C$_1$-C$_8$ haloalkyl;
$R_8$ represents an C$_1$-C$_8$ alkyl, C$_1$-C$_8$ haloalkyl or hydrogen;
$R_{11}$ and $R_{12}$ represent, independently of one another, hydrogen, halogen, CN or NO$_2$;
$R_{13}$ represents a halogen, C$_1$-C$_8$ haloalkyl, C$_1$-C$_8$ haloalkoxy, S(O)$_q$CF$_3$ or SF$_5$;

m, n, q and r represent, independently of one another, an integer equal to 0, 1 or 2;

X represents a trivalent nitrogen atom or a C—$R_{12}$ radical, the three other valencies of the carbon atom forming part of the aromatic ring;

(B) a pharmaceutically effective amount of an ivermectin derivative of the formula (IIb):

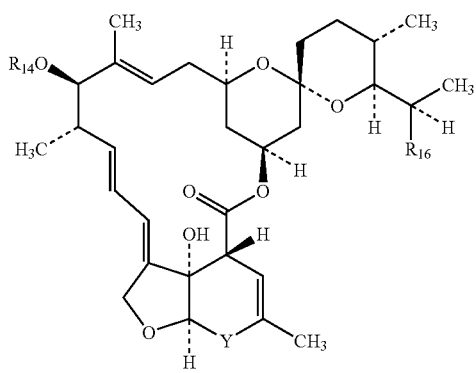

(IIb)

wherein:
$R_{14}$ represents —$(CH_2)_s$—O—Z
wherein,
s is 1 or 2;
Y represents —$CH(OR_{15})$—, —$C(=O)$— or —$C(=NOR_{15})$;
$R_{15}$ represents hydrogen, or $C_1$-$C_8$ alkyl; and
$R_{16}$ represents —$CH_3$ or —$CH_2CH_3$;
Z is $C_1$-$C_8$ alkyl, $C_1$-$C_8$ acyl, or $C_1$-$C_8$ alkylalkoxy,
(C) a pharmaceutically acceptable carrier.

In another embodiment of the invention for the compound of formula (IIb), the composition for the treatment or prophylaxis of parasite infestation in birds or mammals comprises:

(A) a pharmaceutically effective amount of at least one compound of the formula (I)

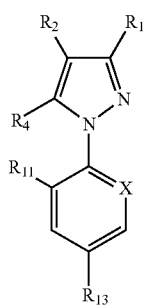

(I)

wherein:
$R_1$ is a halogen, CN or $C_1$-$C_4$ alkyl;
$R_2$ is $S(O)_n R_3$ or $C_1$-$C_4$ haloalkyl;
$R_3$ is $C_1$-$C_4$ alkyl or $C_1$-$C_4$ haloalkyl;
$R_4$ represents a hydrogen, fluorine, chlorine, bromine, $NR_5R_6$, $S(O)_m R_7$, $C(O)R_7$, $C(O)OR_7$, $C_1$-$C_4$ alkyl, $C_1$-$C_4$ haloalkyl, $OR_8$ radical;
$R_5$ and $R_6$ independently represent hydrogen, $C_1$-$C_4$ alkyl, C(O)alkyl; or
$R_7$ represents an $C_1$-$C_4$ alkyl or $C_1$-$C_4$ haloalkyl;
$R_8$ represents an $C_1$-$C_4$ alkyl, $C_1$-$C_4$ haloalkyl or hydrogen;

$R_{11}$ and $R_{12}$ represent, independently of one another, hydrogen, halogen, CN or $NO_2$;
$R_{13}$ represents a halogen, $C_1$-$C_4$ haloalkyl, $C_1$-$C_4$ haloalkoxy, $S(O)_q CF_3$ or $SF_5$;
m, n, q and r represent, independently of one another, an integer equal to 0, 1 or 2;
X represents a trivalent nitrogen atom or a C—$R_{12}$ radical, the three other valencies of the carbon atom forming part of the aromatic ring;

(B) a pharmaceutically effective amount of an ivermectin derivative of the formula (IIa):

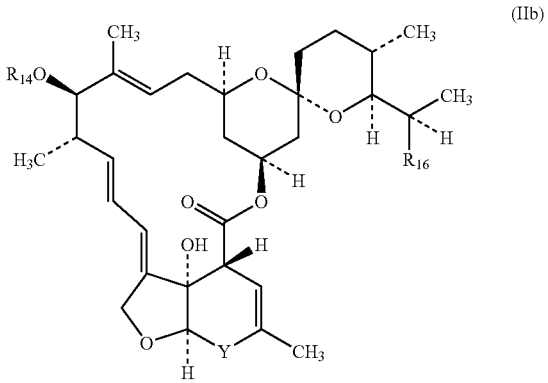

(IIb)

wherein:
$R_{14}$ represents —$(CH_2)_s$—O—Z
wherein,
s is 1;
Y represents —$CH(OR_{15})$—, —$C(=O)$— or —$C(=NOR_{15})$;
$R_{15}$ represents hydrogen, or $C_1$-$C_8$ alkyl; and
$R_{16}$ represents —$CH_3$ or —$CH_2CH_3$;
Z is $C_1$-$C_4$ alkyl, $C_1$-$C_4$ acyl, or $C_1$-$C_4$ alkylalkoxy,
(C) a pharmaceutically acceptable carrier.

In an embodiment of the invention for formula (IIb), the composition for the treatment and prophylaxis of parasite infestation in birds or mammals comprises:

(A) a pharmaceutically effective amount of at least one compound of the formula (I)

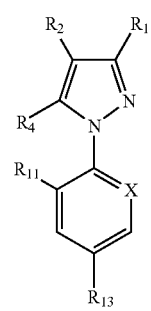

(I)

wherein:
$R_1$ is CN;
$R_2$ is $S(O)_n R_3$;
$R_3$ is $CF_3$;
$R_4$ represents $NR_5R_6$;
$R_5$ and $R_6$ independently represent hydrogen;
$R_{11}$ and $R_{12}$ represent Cl;
$R_{13}$ represents $CF_3$;

n is 1;
X represents C—$R_{12}$
(this compound is also known as fipronil); and
(B) a pharmaceutically effective amount of an ivermectin derivative of the formula (IIb):

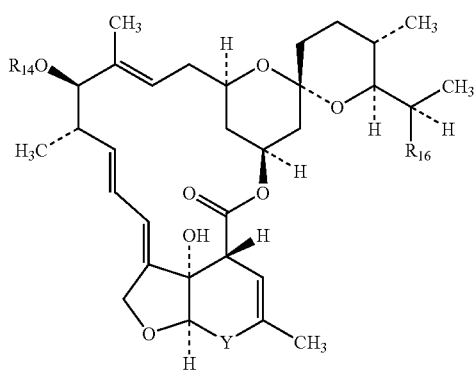

(IIb)

wherein:
$R_{14}$ represents —$(CH_2)_s$—O—Z
wherein,
s is 1;
Y represents —CH($OR_{15}$)—, —C(=O)— or —C(=N$OR_{15}$);
$R_{15}$ represents hydrogen, or $C_1$-$C_8$ alkyl; and
$R_{16}$ represents —$CH_3$ or —$CH_2CH_3$;
Z is $C_1$-$C_4$ alkyl, $C_1$-$C_4$ acyl, or $C_1$-$C_4$ alkylalkoxy,
(C) a pharmaceutically acceptable carrier.

In an embodiment of the invention for formula (IIb), the composition for the treatment and prophylaxis of parasite infestation in birds or mammals comprises:
(A) a pharmaceutically effective amount of at least one compound of the formula (I)

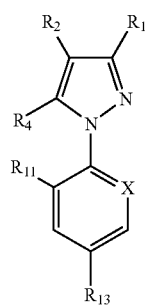

(I)

wherein:
$R_1$ is CN;
$R_2$ is S(O)$_n R_3$;
$R_3$ is $CF_3$;
$R_4$ represents $NR_5 R_6$;
$R_5$ and $R_6$ independently represent hydrogen;
$R_{11}$ and $R_{12}$ represent Cl;
$R_{13}$ represents $CF_3$;
n is 1;
X represents C—$R_{12}$
(this compound is also known as fipronil); and
(B) a pharmaceutically effective amount of an ivermectin derivative of the formula (IV):

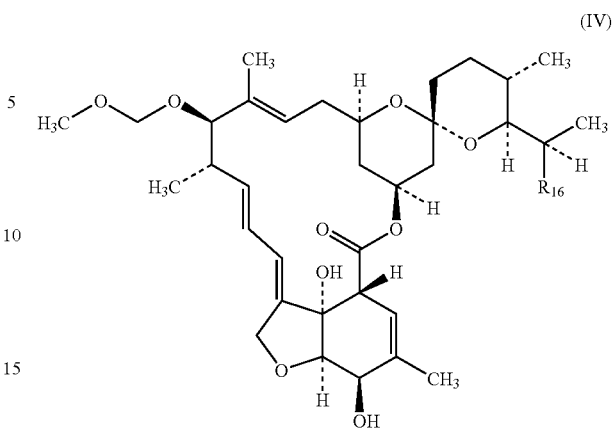

(IV)

wherein:
$R_{16}$ represents —$CH_3$ or —$CH_2CH_3$; and
(C) a pharmaceutically acceptable carrier.

For each of the above embodiments, the pharmaceutically acceptable carrier is selected on the basis of the form of the composition which can include oral formulations, baits, dietary supplements, powders, shampoos, pastes, concentrated solution, suspension, microemulsion and emulsion. Compositions intended for pharmaceutical use may be prepared according to any method known in the art for the manufacture of pharmaceutical compositions. Remington— The Science and Practice of Pharmacy (21$^{st}$ Edition) (2005), Goodman & Gilman's The Pharmacological Basis of Therapeutics (11$^{th}$ Edition) (2005) and Ansel's Pharmaceutical Dosage Forms and Drug Delivery Systems (8$^{th}$ Edition), edited by Allen et al., Lippincott Williams & Wilkins, (2005).

Organic solvents for the pharmaceutically acceptable carrier unless otherwise specified includes the commonly acceptable organic solvents known in the formulation art. These solvents may be found, for example, in Remington Pharmaceutical Science, 16$^{th}$ Edition (1986). These solvents include, for example, acetone, ethyl acetate, methanol, ethanol, isopropanol, dimethylformamide, dichloromethane or diethylene glycol monoethyl ether (Transcutol). These solvents can be supplemented by various excipients according to the nature of the desired phases, such as $C_8$-$C_{10}$ caprylic/capric triglyceride (Estasan or Miglyol 812), oleic acid or propylene glycol.

The pharmaceutical carrier may also comprise a microemulsion. Microemulsions are also well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

The oily phase can in particular be formed from mineral or vegetable oils, from unsaturated polyglycosylated glycerides or from triglycerides, or alternatively from mixtures of such compounds. The oily phase preferably comprises triglycerides and more preferably medium-chain triglycerides, for example $C_8$-$C_{10}$ caprylic/capric triglyceride. The oily phase will represent, in particular, from about 2 to about 15%, more particularly from about 7 to about 10%, preferably from about 8 to about 9%, V/V of the microemulsion.

The aqueous phase includes, for example water or glycol derivatives, such as propylene glycol, glycol ethers, polyethylene glycols or glycerol. Propylene glycol, diethylene glycol monoethyl ether and dipropylene glycol monoethyl ether are especially preferred. Generally, the aqueous phase will represent a proportion from about 1 to about 4% V/V in the microemulsion. Surfactants for the microemulsion include diethylene glycol monoethyl ether, dipropylene glycol monomethyl ether, polyglycolysed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. The cosurfactant to surfactant ratio will preferably be from about 1/7 to about 1/2. There will preferably be from about 25 to about 75% V/V of surfactant and from about 10 to about 55% V/V of cosurfactant in the microemulsion.

In one embodiment of the invention, the composition can be in ready-to-use solution form as is described in U.S. Pat. No. 6,395,765. In addition to the compound of formula (I) and formula (II), the ready-to-use solution can contain a crystallization inhibitor, an organic solvent and an organic co-solvent.

In another embodiment of the ready-to-use solution, the crystallization inhibitor is present, in particular, in a proportion of from 1 to 20% (W/V), preferably from 5 to 15%, this inhibitor satisfying the test according to which: 0.3 ml of a solution A comprising 10% (W/V) of the compound of formula (I) in the organic solvent defined below, and 10% of this inhibitor, are placed on a glass slide at 20° C. for 24 hours, after which few or no crystals, in particularly fewer than 10 crystals, preferably 0 crystals, are seen with the naked eye on the glass slide; the organic solvent has a dielectric constant of between 10 and 35, preferably of between 20 and 30, the content of this organic solvent in the overall composition preferably representing the complement to 100% of the composition; and the organic co-solvent having a boiling point below 100° C., preferably below 80° C., and having a dielectric constant of between 10 and 40, preferably of between 20 and 30; this co-solvent may advantageously be present in the composition in a organic co-solvent/organic solvent weight/weight (W/W) ratio of between 1/15 and 1/2. The solvent is volatile so as to act in particular as a drying promoter, and is miscible with water and/or with the organic solvent.

The crystallization inhibitor can in particular be present in a proportion of about 1 to about 20% (W/V), preferably of about 5 to about 15%. The inhibitor preferably corresponds to the test in which 0.3 ml of a solution comprising 10% (W/V) of the compound of formula (I) in the liquid carrier and 10% of the inhibitor are deposited on a glass slide at 20° C. and allowed to stand for 24 hours. The slide is then observed with the naked eye. Acceptable inhibitors are those whose addition provides for few or no crystals, and in particular less than 10 crystals, preferably 0 crystals.

The formulation can also comprise an antioxidizing agent intended to inhibit oxidation in air, this agent being in particular present in a proportion of about 0.005 to about 1% (W/V), preferably of about 0.01 to about 0.05%.

Crystallization inhibitors which can be used in the invention include:

polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; sodium abietate; alkyl sulphates, in particular sodium lauryl sulphate and sodium cetyl sulphate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, or preferably a mixture of at least two of the compounds listed above.

In a particularly preferred embodiment, a crystallization inhibitor pair will be used. Such pairs include, for example, the combination of a film-forming agent of polymeric type and of a surface-active agent. These agents will be selected in particular from the compounds mentioned above as crystallization inhibitor.

Particularly preferred film-forming agents of polymeric type include:
the various grades of polyvinylpyrrolidone,
polyvinyl alcohols, and
copolymers of vinyl acetate and of vinylpyrrolidone.

Especially preferred surface-active agents, include those made of non-ionic surfactants, preferably polyoxyethylenated esters of sorbitan and in particular the various grades of polysorbate, for example Polysorbate 80.

The film-forming agent and the surface-active agent can in particular be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the fur, that is to say without a tendency towards sticking or towards a sticky appearance, despite the high concentration of active material.

Particularly preferred antioxidizing agents are those conventional in the art and include, for example, butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied can be of the order of about 0.3 to about 1 ml, preferably of the order of about 0.5 ml, for cats and of the order of about 0.3 to about 3 ml for dogs, depending on the weight of the animal.

In another embodiment of the invention, the composition can be in pour-on form as described in U.S. Pat. No. 6,010, 710. The pour-on formulations, which are advantageously oily, generally comprise a diluent or vehicle and also a solvent (organic solvent) for the compound of formula (I) if the latter is not soluble in the diluent.

As organic solvent which can be used in the invention, mention may be made in particular of: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol and diethyl phthalate, or a mixture of at least two of these solvents.

As vehicle or diluent, mention may be made in particular of plant oils such as soybean oil, groundnut oil, castor oil, corn oil, cotton oil, olive oil, grape seed oil, sunflower oil, etc.; mineral oils such as petrolatum, paraffin, silicone, etc.; aliphatic or cyclic hydrocarbons or alternatively, for example, medium-chain ($C_8$ to $C_{12}$ in particular) triglycerides.

An emollient and/or spreading and/or film-forming agent will preferably be added, this agent being selected in particular from:
(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils, in particular polydimethylsiloxane (PDMS) oils, for example those containing silanol functionalities, or a 45V2 oil,
(b) anionic surfactants such as alkaline stearates, in particular sodium, potassium or ammonium stearates; calcium stearate, triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil,
(c) cationic surfactants such as water-soluble quaternary ammonium salts of formula N.sup.+R'R"R'"R"", $Y^{-0}$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used,
(d) amine salts of formula $N^+R'R"R'"$ in which the radicals R are optionally hydroxylated hydrocarbon radicals; octadecylamine hydrochloride is among the cationic surfactants which can be used,
(e) nonionic surfactants such as sorbitan esters, which are optionally polyoxyethylenated, in particular polysorbate 80, polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide,
(f) amphoteric surfactants such as the substituted lauryl compounds of betaine; or
(g) a mixture of at least two of these agents.

The solvent will be used in proportion with the concentration of the compound I and its solubility in this solvent. For example, fipronil has a solubility of 4.3% m/V in acetyl tributyl citrate. It will be sought to have the lowest possible volume. The vehicle makes up the difference to 100%.

The emollient is preferably used in a proportion of from 0.1 to 10%, in particular from 0.25 to 5%, by volume.

In another embodiment of the invention, the composition can be in spot-on form. For spot-on formulations, the carrier can be a liquid carrier vehicle as described in U.S. Pat. No. 6,426,333 which comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.

The liquid carrier vehicle can optionally contain a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

In another embodiment of the invention, the composition can be in paste form. One embodiment of a paste form is described in U.S. Pat. No. 6,787,342, which is hereby incorporated by reference. In addition to the 1-N-phenylpyrazole and ivermectin derivative compound described above, the paste also contains fumed silica; a viscosity modifier; a carrier; optionally, an absorbent; and optionally, a colorant, stabilizer, surfactant, or preservative.

The process for preparing a paste formulation comprises the steps of:
(a) dissolving or dispersing the 1-N-phenylpyrazole and ivermectin derivative compound into the carrier by mixing;
(b) adding the fumed silica to the carrier containing the dissolved 1-N-phenylpyrazole and ivermectin derivative compound and mixing until the silica is dispersed in the carrier;
(c) allowing the intermediate formed in (b) to settle for a time sufficient in order to allow the air entrapped during step (b) to escape; and (d) adding the viscosity modifier to the intermediate with mixing to produce a uniform paste.

The steps are illustrating, but not limiting. For example, step (a) can be moved to the last step.

Another embodiment of the paste of the invention contains 1-N-phenylpyrazole and ivermectin derivative compound, fumed silica, a viscosity modifier, an absorbent, a colorant; and a hydrophilic carrier which is triacetin, a monoglyceride, a diglyceride, or a triglyceride.

Further embodiments of the paste include but are not limited to pastes wherein the viscosity modifier is selected from the group consisting of PEG 200, PEG 300, PEG 400, PEG 600, monoethanolamine, triethanolamine, glycerol, propylene glycol, polyoxyethylene (20) sorbitan mono-oleate (polysorbate 80 or Tween 80), and polyoxamers (e.g., Pluronic L 81); the absorbent is selected from the group consisting of magnesium carbonate, calcium carbonate, starch, and cellulose and its derivatives; and the colorant is selected from the group consisting of titanium dioxide iron oxide, and FD&C Blue #1 Aluminum Lake.

The phenylpyrazoles as a class are known in the art and are described, for example in U.S. Pat. Nos. 5,885,607; 6,010,710; 6,083,519; 6,096,329; 6,395,765 and 6,867,229 (all assigned to Merial, Ltd.) as well as in U.S. Pat. Nos. 5,576,429; 5,122,530, and EP 295 177, the disclosures of which, as well as the references cited herein, are incorporated by reference. This class of insecticides is known to possess excellent activity against insects such as ticks and fleas.

Ivermectins are recognized as being part of a broader class of compounds known as the macrocyclic lactones. For each of the above embodiments of the invention, an additional macrocylic lactone can be added to the composition. Examples of such macrocyclic lactones include but are not limited to avermectins such as abamectin, doramectin, emamectin, eprinomectin, ivermectin, latidectin, lepimectin, selamectin and milbemycins such as milbemectin, milbemycin D and moxidectin. Also included are the 5-oxo and 5-oxime derivatives of said avermectins and milbemycins.

These previously known macrocyclic lactone compounds can easily be obtained either commercially or through techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may in particular be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 677,054.

Macrocyclic lactones are either natural products or are semi-synthetic derivatives thereof. The structure of the avermectins and milbemycins are closely related, e.g., by sharing a complex 16-membered macrocyclic lactone ring; milbemycins lack the glycosidic moiety of the avermectins. The natural product avermectins are disclosed in U.S. Pat. No. 4,310,519 to Albers-Schönberg, et al., and the 22,23-dihydro avermectin compounds are disclosed in Chabala, et al., U.S. Pat. No. 4,199,569. Mention is also made of Kitano, U.S. Pat. No. 4,468,390, Beuvry et al., U.S. Pat. No. 5,824,653, European Patent Application 0 007 812 A1, published Jun. 2, 1980, U.K. Patent Specification 1 390 336, published Apr. 9, 1975, European Patent Application 0 002 916 A2, and Ancare New Zealand Patent No. 237 086, inter alia. Naturally occurring milbemycins are described in Aoki et al., U.S. Pat. No. 3,950,360 as well as in the various references cited in "The Merck Index" $_{12}$th ed., S. Budavari, Ed., Merck & Co., Inc. Whitehouse Station, New Jersey (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859, 657, 4,963,582, 4,855,317, 4,871,719, 4,874,749, 4,427,663, 4,310,519, 4,199,569, 5,055,596, 4,973,711, 4,978,677, 4,920,148 and EP 667,054.

For each of the above embodiments, a cestodal agent may be added which include but are not limited to praziquantel, pyrantel, espirantel, niclosamide, mebendazole, albendazole, triclabendazole, metrifonate oxamniquine and morantel. In one embodiment of the invention, at least one additional macrocyclic lactone and/or cestodal agent is added to the composition and the macrocyclic lactone is eprinomectin and the cestodal agent is praziquantel.

For each of the above embodiments, a nitroguanidine or pyridylmethylamine insecticide may be added. These insecticides include but are not limited to clothiandin, dinotefuran, imidacloprid, thiamethoxam, acetamiprid, nitepyram and thiacloprid.

Also contemplated are the pharmaceutically acceptable acid or base salts, where applicable, of the 1-N-phenylpyrazoles and macrolide lactones provided for herein. The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids tricarboxylic acids and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

The subject of the present invention is also a process for the elimination of parasites in mammals and birds, especially dogs and cats, using a composition according to the present invention.

In one embodiment of the invention, direct pour-on skin formulation according to the present invention can obtain long-lasting and broad-spectrum efficacy when the solution is applied to the animal's back, preferably along the line of the back at one or more points.

According to a first embodiment for administering direct pour-on formulations, the process consists in applying the solution to the animals in pasture and/or before they arrive in pasture, the application preferably being repeated every month, preferably every two months.

According to a second embodiment for administering direct pour-on formulation, the process consists in applying the solution to livestock animals before they arrive in the "Feed Lot", it being possible for this application to be the final one before the animals are slaughtered.

Obviously, the process may also consist in combining these two embodiments, namely the first followed by the second.

The solutions according to the invention may be applied using any means known per se, preferably using an applicator gun or a metering flask.

This method serves to cleanse the skin and the hairs of the animals by eliminating the parasites which are present thereon, as well as their residues and dejections. The result of this is that the animals are no longer stressed by the parasites and their bites, this having positive consequences, for example on their growth and on the use of their food ration.

In another embodiment of the invention, application of spot-on formulation according to the present invention can also obtain long-lasting and broad-spectrum efficacy when the solution is applied to the mammal or bird.

Administration of the spot-on formulation may be intermittent in time and may be administered daily, weekly, biweekly, monthly, bimonthly, quarterly, or even for longer durations of time. The time period between treatments depends upon factors such as the parasite(s) being treated, the degree of infestation, the type of mammal or bird and the environment where it resides. It is well within the skill level of the practitioner to determine a specific administration period for a particular situation. This invention contemplates a method for permanently combating a parasite in an environment in which the animal is subjected to strong parasitic pressure where the administration is at a frequency far below a daily administration in this case. For example, it is preferable for the treatment according to the invention to be carried out monthly on dogs and on cats.

The administration of spot-on formulations also provides for a method for cleaning the coats and the skin of animals by removal of the parasites which are present and of their waste and excreta. The animals treated thus exhibit a coat which is more pleasing to the eye and more pleasant to the touch.

While not wishing to be bound by theory, it is believed that the invention spot-on formulation work by the dose dissolving in the natural oils of the host's skin, fur or feathers. From there, the therapeutic agent(s) distribute around the host's body through the sebaceous glands of the skin. The therapeutic agent also remains in the sebaceous glands. Thus, the glands provide a natural reservoir for the therapeutic agent which allows for the agent to be drained back out to the follicles to reapply itself to the skin and hair. This, in turn, provides for longer time periods between application as well as not having to re-administer the dose after the host becomes wet because of rain, bathes, etc. Moreover, the inventive formulation have the further advantage in self-grooming animals of not being directly deposited of the skin or fur where the animals could orally ingest the therapeutic agent, thereby becoming sick or possibly interacting with other therapeutic agent being orally administered.

Other routes of administration include paste formulation, oral drench formulation, chewable formulation, transdermal or transmucosal patch or liquid, gel or paste, solution for inhalation and injectable formulation.

In another preferred embodiment this provides for a composition for combating fleas in small mammals, in particular dogs and cats, characterized in that it contains at least one compound (A) of formula (I) as defined above and at least one endectocidal compound (B), in amounts and proportions having a parasitical effectiveness for fleas and worms, in a vehicle acceptable for the animal.

The compounds (A) and (B) may be administered continuously, particularly for prophylaxis, by known methods. Generally, a dose of from about 0.001 to about 10 mg per kg of body weight given as a single dose or in divided doses for a period of from 1 to 5 days will be satisfactory but, of course, there can be instance where higher or lower dosage ranges are indicated and such are within the scope of this invention. It is well within the routine skill of the practitioner to determine a particular dosing regimen for a specific host and parasite.

Preferably, a single formulation containing the compounds (A) and (B) in a substantially liquid carrier and in a form which makes possible a single application, or an application repeated a small number of times, will be administered to the animal over a highly localized region of the animal, preferably between the two shoulders. Remarkably, it has been discovered that such a formulation is highly effective against both the targeted ectoparasites and the targeted endoparasites.

The treatment is preferably carried out so as to administer to the host, on a single occasion, a dose containing between about 0.001 and about 100 mg/kg of derivative (A) and containing between about 0.1 and about 2000 µg/kg, more preferably 1000 µg/kg of compound of type (B), in particular in the case of a direct topical administration.

The amount of compound (A) for birds and animals which are small in size is preferably greater than about 0.01 mg and in a particularly preferred way between about 1 and about 50 mg/kg of weight of animal.

The effective amount in a dose is, for the compound (A), preferably between about 0.001, preferentially about 0.1, and about 100 mg and in a particularly preferred way from about 1 to about 50 mg/kg of weight of animal, the higher amounts being provided for very prolonged release in or on the body of the animal.

The effective amount of compounds (B) in a dose is preferably between about 0.1 µg, preferentially about 1 µg, and about 10 mg and in a particularly preferred way from about 5 to about 200 µg/kg of weight of animal. Especially preferred is a dose between about 0.1 to about 10 mg/kg of weight of animal, with about 0.5 to 6 mg/kg being most especially preferred. The proportions, by weight, of compound (A) and of compound (B) are preferably between about 5/1 and about 10,000/1.

In a separate embodiment of the invention, novel ivermectin derivative compounds of the formula (II) are provided:

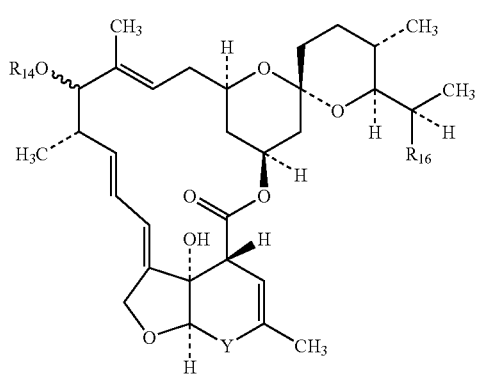

(II)

wherein:

$R_{14}$ represents —$(CH_2)_s$—O—Z
  wherein,
  s is 1 or 2;
Y represents —CH(OR$_{15}$)—, —C(=O)— or —C(=NOR$_{15}$);
$R_{15}$ represents hydrogen, alkyl or phenyl; and
$R_{16}$ represents —$CH_3$ or —$CH_2CH_3$;
Z is alkyl, alkenyl, alkynyl, acyl, alkylalkoxy, aryl, alkanoyloxy, alkoxycarbonyl, alkenoyl, alkynoyl, or aroyl.

In another embodiment of the invention for compound of formula (II) are provided:

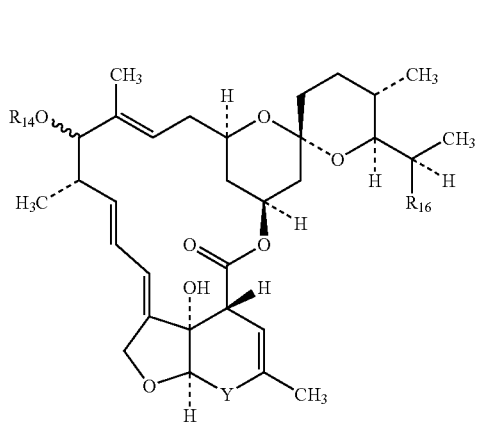

(II)

wherein:

$R_{14}$ represents —$(CH_2)_s$—O—Z
  wherein,
  s is 1 or 2;
Y represents —CH(OR$_{15}$)—, —C(=O)— or —C(=NOR$_{15}$);
$R_{15}$ represents hydrogen, or $C_1$-$C_8$ alkyl; and
$R_{16}$ represents —$CH_3$ or —$CH_2CH_3$;
Z is $C_1$-$C_8$ alkyl, $C_1$-$C_8$ acyl, or $C_1$-$C_8$ alkylalkoxy.

In another embodiment of the invention for compound of formula (II) are provided:

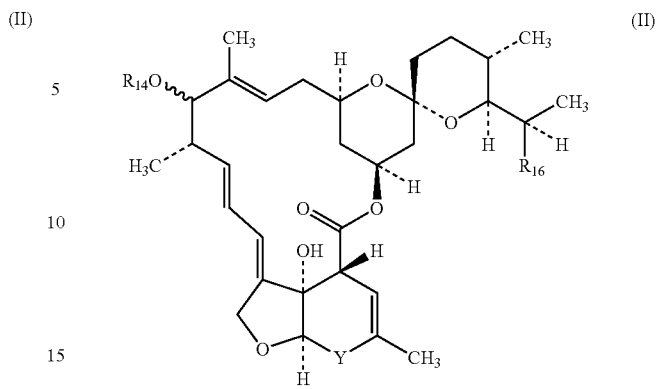

(II)

wherein:

$R_{14}$ represents —$(CH_2)_s$—O—Z
  wherein,
  s is 1;
Y represents —CH(OR$_{15}$)—, —C(=O)— or —C(=NOR$_{15}$);
$R_{15}$ represents hydrogen, or $C_1$-$C_8$ alkyl; and
$R_{16}$ represents —$CH_3$ or —$CH_2CH_3$;
Z is $C_1$-$C_4$ alkyl, $C_1$-$C_4$ acyl, or $C_1$-$C_4$ alkylalkoxy.

In another embodiment of the invention for compound of formula (II) are provided:

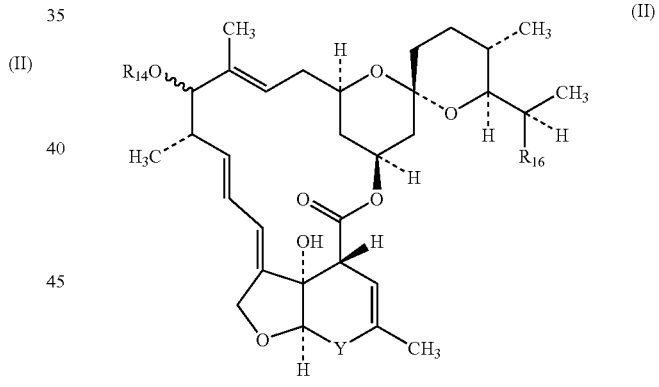

(II)

wherein:

$R_{14}$ represents —$(CH_2)_s$—O—Z
  wherein,
  s is 1;
Y represents —CH(OR$_{15}$)—, —C(=O)— or —C(=NOR$_{15}$);
$R_{15}$ represents hydrogen, or $C_1$-$C_8$ alkyl; and
$R_{16}$ represents —$CH_3$ or —$CH_2CH_3$;
Z is $C_1$-$C_4$ alkyl, $C_1$-$C_4$ acyl, or $C_1$-$C_4$ alkylalkoxy.

In another embodiment of the invention for compound of formula (IIa) are provided:

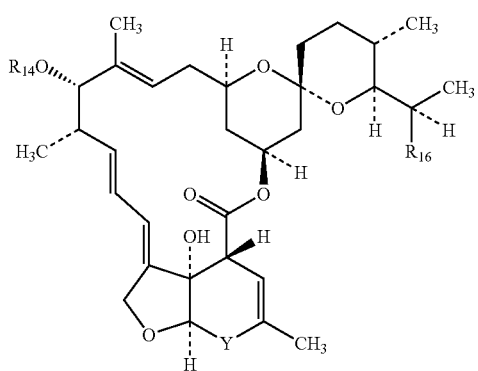

(IIa)

wherein:

$R_{14}$ represents —$(CH_2)_s$—O—Z wherein, s is 1 or 2;

Y represents —$CH(OR_{15})$—, —C(=O)— or —$C(=NOR_{15})$;

$R_{15}$ represents hydrogen, $C_1$-$C_4$ alkyl or phenyl; and $R_{16}$ represents —$CH_3$ or —$CH_2CH_3$;

Z is alkyl, alkenyl, alkynyl, acyl, alkylalkoxy, aryl, alkanoyloxy, alkoxycarbonyl, alkenoyl, alkynoyl, or aroyl.

In another embodiment of the invention for compound of formula (IIa) are provided:

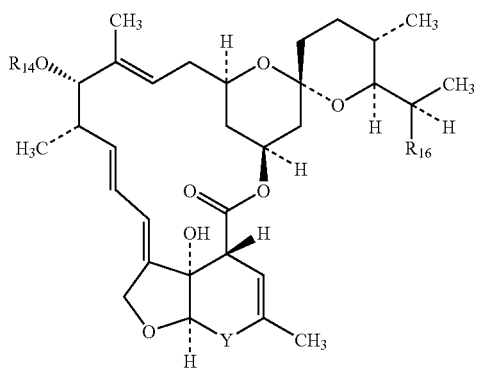

(IIa)

wherein:

$R_{14}$ represents —$(CH_2)_s$—O—Z wherein, s is 1 or 2;

Y represents —$CH(OR_{15})$—, —C(=O)— or —$C(=NOR_{15})$;

$R_{15}$ represents hydrogen, or $C_1$-$C_8$ alkyl; and $R_{16}$ represents —$CH_3$ or —$CH_2CH_3$;

Z is $C_1$-$C_8$ alkyl, $C_1$-$C_8$ acyl, or $C_1$-$C_8$ alkylalkoxy, (C) a pharmaceutically acceptable carrier.

In another embodiment of the invention for compound of formula (IIa) are provided:

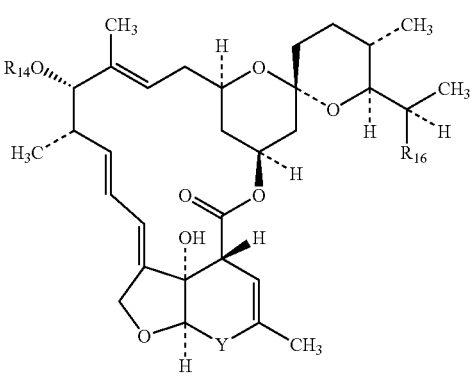

(IIa)

wherein:

$R_{14}$ represents —$(CH2)_s$—O—Z wherein, s is 1;

Y represents —$CH(OR_{15})$—, —C(=O)— or —$C(=NOR_{15})$;

$R_{15}$ represents hydrogen, or $C_1$-$C_8$ alkyl; and $R_{16}$ represents —$CH_3$ or —$CH_2CH_3$;

Z is $C_1$-$C_4$ alkyl, $C_1$-$C_4$ acyl, or $C_1$-$C_4$ alkylalkoxy, (C) a pharmaceutically acceptable carrier.

In another embodiment of the invention for compound of formula (IIa) are provided which has the formula (III):

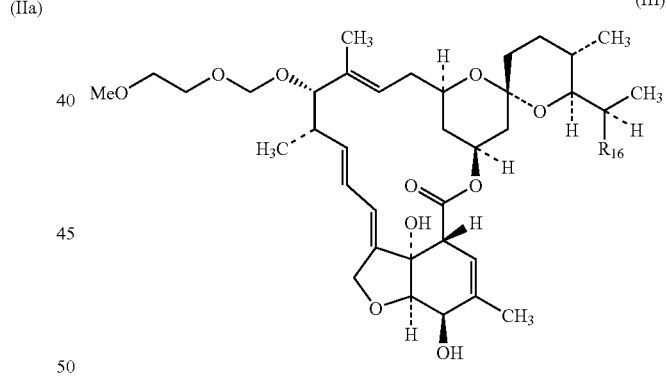

(III)

wherein:

$R_{16}$ represents —$CH_3$ or —$CH_2CH_3$.

In another embodiment of the invention for compound of formula (IIb) are provided:

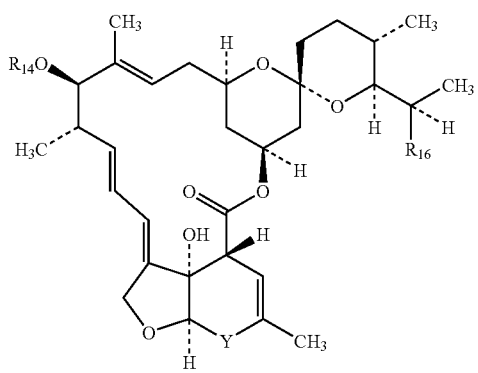

(IIb)

wherein:
$R_{14}$ represents —$(CH_2)_s$—O—Z
  wherein,
  s is 1 or 2;
Y represents —CH(OR$_{15}$)—, —C(=O)— or —C(=NOR$_{15}$);
$R_{15}$ represents hydrogen, $C_1$-$C_4$ alkyl or phenyl; and
$R_{16}$ represents —$CH_3$ or —$CH_2CH_3$;
Z is alkyl, alkenyl, alkynyl, acyl, alkylalkoxy, aryl, alkanoyloxy, alkoxycarbonyl, alkenoyl, alkynoyl, or aroyl.

In another embodiment of the invention for compound of formula (IIb) are provided:

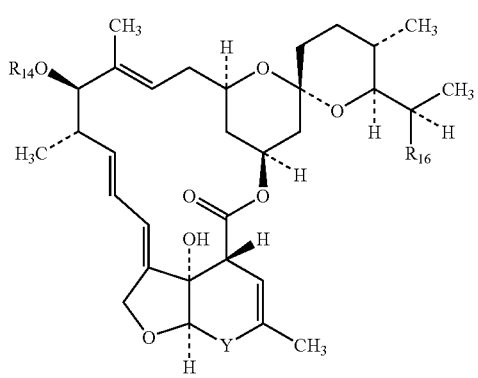

(IIb)

wherein:
$R_{14}$ represents —$(CH_2)_s$—O—Z
  wherein,
  s is 1 or 2;
Y represents —CH(OR$_{15}$)—, —C(=O)— or —C(=NOR$_{15}$);
$R_{15}$ represents hydrogen, or $C_1$-$C_8$ alkyl; and
$R_{16}$ represents —$CH_3$ or —$CH_2CH_3$;
Z is $C_1$-$C_8$ alkyl, $C_1$-$C_8$ acyl, or $C_1$-$C_8$ alkylalkoxy.

In another embodiment of the invention for compound of formula (IIb) are provided:

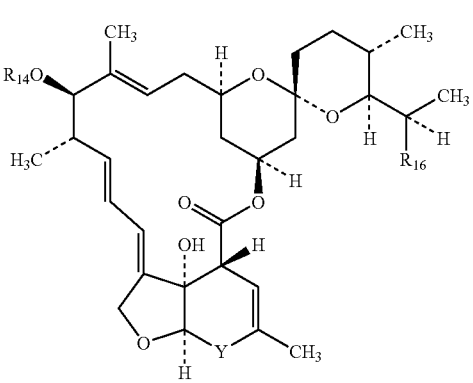

(IIb)

wherein:
$R_{14}$ represents —$(CH_2)_s$—O—Z
  wherein,
  s is 1;
Y represents —CH(OR$_{15}$)—, —C(=O)— or —C(=NOR$_{15}$);
$R_{15}$ represents hydrogen, or $C_1$-$C_8$ alkyl; and
$R_{16}$ represents —$CH_3$ or —$CH_2CH_3$;
Z is $C_1$-$C_4$ alkyl, $C_1$-$C_4$ acyl, or $C_1$-$C_4$ alkylalkoxy.

In another embodiment of the invention for compound of formula (IIb) are provided which has the formula (IV):

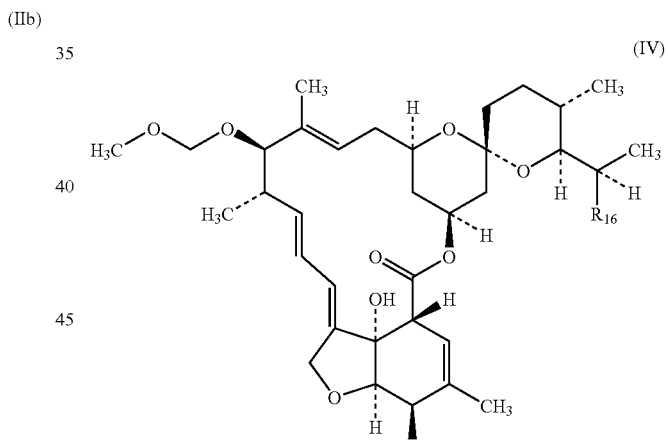

(IV)

wherein:
$R_{16}$ represents —$CH_3$ or —$CH_2CH_3$.

Another embodiment of the invention is the process for making the novel ivermectin derivatives of the invention. Ivermectin is a mixture of two homologous compounds, the B1a and the B1b form:

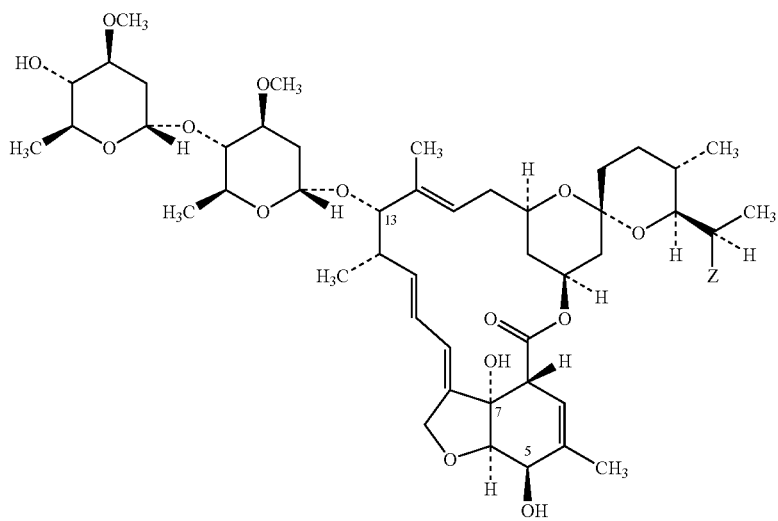

$B_{1a}$=Z=CH$_2$CH$_3$
$B_{1b}$=Z=CH$_3$

The process of making the novel ivermectin derivative compounds of the invention comprises:
(a) cleaving the disaccharide the C-13 position of ivermectin resulting in an —OH at C-13;
(b) protecting the —OH groups at C-5, C-7 and C-13;
(c) selectively deprotecting the protected —OH groups at C-13;
(d) alkylating the deprotected —OH to form the moiety —(CH$_2$)$_s$(OCH$_2$)$_t$O-alkyl or —(CH$_2$)$_s$(OCH$_2$CH$_2$)$_u$O-alkyl, wherein s, t and u are as defined above;
(e) purifying the product formed from step (d);
(f) deprotecting the protected —OH groups at C-7 and C-13 and purifying the resulting compound; and
(g) optionally performing one of the following additional steps (i)-(iii):
  (i) alkylating the —OH at C-5;
  (ii) oxidizing the —OH at C-5 to form a 5-oxo compound;
  (iii) oxidizing the —OH at C-5 to form a 5-oxo compound and optionally further reacting the 5-oxo compound with a hydroxylamine to form a 5-oxime compound and further optionally alkylating the —OH of the 5-oxime moiety.

In another embodiment of the invention for the process for making the novel ivermectin derivatives of the invention, the process steps comprise:
(a) cleaving by acid catalyzed hydrolysis the disaccharide the C-13 position of ivermectin resulting in an —OH at C-13;
(b) protecting the —OH groups at C-5, C-7 and C-13 with a first protection step of reacting the —OH groups with t-butyldimethylsilylchloride (TBDMS) followed by a second protection step of reacting the TBDMS protected hydroxyl groups with trimethylsilyl chloride (TMS) to obtain a C-7 and C-13 TMS protected hydroxyl and a C-5 TBDMS protected hydroxyl;
(c) selectively deprotecting the C-13 TMS protected hydroxyl group by a reaction with dichloroacetic acid;
(d) alkylating the deprotected —OH with 2-methoxyethoxymethyl chloride (MEM chloride) to form the moiety —CH$_2$—OCH$_2$CH$_2$—O—CH$_3$;
(e) purifying the product formed from step (d) via crystallization; and
(f) deprotecting the protected —OH groups at C-7 and C-13 and purifying the resulting compound by crystallization.

Cleavage of the disaccharide can occur by any means known to those of skill in the art, e.g. acid or base catalyzed hydrolysis/solvolysis. Selection of appropriate protecting groups for selective protection of hydroxyl groups is well known in the art (see e.g. *Protective Groups in Organic Synthesis, Third Edition*—Chapter 2—"Protection for the Hydroxyl Group, Including 1,2- and 1,3-Diols", Green and Wuts, John Wiley and Sons, pages 17-245, (1999)) and easily practiceable by those of ordinary skill in the art. Purification can be accomplished by any known means in the art including HPLC, crystallization, etc. The optional steps (i)-(iii) can be performed using the techniques described in U.S. Pat. No. 5,015,630 which is incorporated herein by reference.

Other advantages and characteristics of the invention will become apparent on reading the following description, given by way of non-limiting examples.

EXAMPLES

Example 1

Synthetic Procedure for Making a MEM Derivative of Ivermectin

The MEM derivative of ivermectin has the following formula:

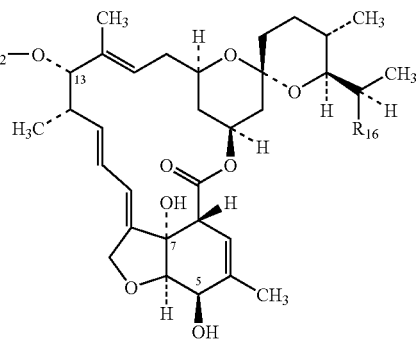

wherein $R_{16}$=—$CH_2CH_3$ for the B1a form and $R_{15}$=—$CH_3$ for the B1b form.

In order to synthesize the MEM derivative of ivermectin, the disaccharide moiety at the C-13 position of ivermectin is cleaved by acid solvolysis using a 1% acid solution to effect cleavage to the ivermectin aglycone. The —OH groups at C-5, C-7 and C-13 are then protected with t-butyldimethyl-silyl chloride (TBDMS) and then subsequently protected with trimethylsilyl chloride (TMS) to obtain the 7,13-bis-O-TMS-5-O-TBDMS ivermectin aglycone.

The 7,13-bis-O-TMS-5-O-TBDMS ivermectin aglycone is then selectively deprotected using dichloroacetic acid to obtain the 7-O-TMS-5-O-TBDMS ivermectin aglycone. This aglycone is then alkylated with 2-methoxyethoxymethyl chloride (MEM chloride) and subsequently purified via crystallization to obtain the 13-MEM-7-O-TMS-5-O-TBDMS ivermectin aglycone.

The 13-MEM-7-O-TMS-5-O-TBDMS ivermectin aglycone is deprotected to remove the remaining silyl groups and purified by crystallization from isopropanol to produce an isopropanol solvate of the MEM derivative of ivermectin. The resulting MEM derivative of ivermectin is obtained in an overall yield of about 65%.

Synthetic procedures for making ivermectin MEM derivatives are known to one of skill in the art. For example, see Cvetovich et al, *J. Org. Chem.* 62: 3989-3993 (1997), the contents of which is herein incorporated in its entirety.

Example 2

Efficacy of MEM Derivatives of Ivermectin Against Fleas

Two Ivermectin derivatives (Formula (III) and Formula (IV)) were tested for their efficacy against fleas on male dogs. Twenty female and 16 male dogs of various breeds and weighing 9.3 to 21.6 kg were used to show the efficacy of compounds of formula (III) and Formula (IV) against fleas. Dogs were allocated to treatment by restricted randomization based on pretreatment (Day 0) flea count. Treatments were vehicle control, compound of Formula (III) in a 1.5% or 2.5% solution applied topically at 1 ml/kg to provide a dose of 15 or 25 mg/kg, compound of Formula IV in a 1% or 1.5% solution applied topically at 1 ml/kg to provide a dose of 10 or 15 mg/kg. Dogs were housed individually in cages or indoor runs. Each dog was infested with 100 fleas (*Ctenocephalides felis*) on Days −1, 13, 20 and 27. Flea counts were performed by manually parting the dog's hair and counting the number of live fleas observed (so-called "thumb counting") on Days 0, 1, 2, 3, 14, 15, 16, 21, 22, 23, 28, 29, 30 and 31. After the Day 31 thumb count, each dog's hair was thoroughly combed, and the number of live fleas picked up by the comb was recorded ("comb counting").

Flea counts from dogs treated with 15 mg/kg of either compound of Formula (III) or compound of Formula (IV) were significantly ($p<0.05$) lower than control counts on all posttreatment counting days except Day 1. There was never any significant difference between compound of Formula (III) at 25 mg/kg and compound of Formula (IV) at 15 mg/kg. The group treated with 15 mg/kg compound of Formula (III) had significantly ($p<0.05$) higher flea counts on Days 1, 22, 23 and 31 (comb counts) than the group treated with 10 mg/kg compound of Formula (IV), and had significantly ($p<0.05$) higher flea counts on Days 30 and 31 (thumb counts) than the group treated with 15 mg/kg of the compound of Formula (IV). Percentage reductions from control based on Day 31 comb counts ranged from 46.9% for 15 mg/kg compound of Formula (III) to 89.1% for 10 mg/kg compound of Formula (IV).

Example 3

Efficacy of MEM Derivatives of Ivermectin Against Sarcoptic Mangae

Two Ivermectin derivatives (Formula (III) and Formula (IV)) were tested for their efficacy against Sarcoptic Mange on male dogs. Twenty-three crossbred dogs and one Heeler (Australian Cattle Dog), weighing 2.9 to 20.0 kg, with estimated ages ranging from 3 months old to 7 years, and naturally infested with *Sarcoptes scabiei* var *canis*, were used to compare the efficacy of compounds of formulas (III) and formula (IV) applied topically according to the multiple point application system. There were 12 male dogs and 12 female dogs.

Dogs were individually kennelled. Replicates of four dogs were formed based on animal availability and mite counts; within replicates, dogs were randomly allocated to a vehicle-treated (L-930,870) group or groups which received compound of Formula (III) at 15 mg/kg body weight or compound of Formula IV at either 10 mg/kg or 15 mg/kg at a dose volume of 1 ml/kg. The investigator was blinded to the treatment code. All treatments were applied topically on Day 0. Mite numbers were assessed on Days −1 or 0, 7, 14, 28, 42, and 56.

Mites were recovered throughout the trial from 4 of 6 animals in the vehicle-treated group. On and after Day 28, no mites were found on any of the six dogs treated with compound of Formula (III) at 15 mg/kg. Dogs treated with compound of Formula (III) or with compound of Formula (IV) had significantly ($p<0.05$) fewer live mites than the control dogs at each post-treatment observation time.

Example 4

Efficacy of MEM Derivatives of Ivermectin Against Hook- and Roundworms

A study was conducted to compare the activity of 15 mg of compound of Formula (III)/kg of body weight and both 10 and 15 mg compound of Formula (IV)/kg of body weight for topical use against hookworm and ascarid infections in dogs. Infections were induced in 13 male and 11 female beagle pups by administering 800 larvated eggs of *Toxocara canis* and 150 larvae of *Ancylostoma caninum* orally on Day −47. The pups were 15 to 16 weeks old and weighed 4.1 to 5.8 kg. After infections of both parasites became patent, pups were allocated to six replicates of four pups each based on Day −1 hookworm fecal egg-per-gram counts. Within a replicate, pups were randomly assigned to one of four coded treatment groups (1-4). The treatments were as follows:
1) Vehicle control, 1 ml/kg body weight;
2) Compound of Formula (III), 1.5% sol., 1 ml/kg, 15 mg/kg body weight;
3) Compound of Formula (IV), 1.0% sol., 1 ml/kg, 10 mg/kg body weight; and
4) Compound of Formula (IV), 1.5% sol., 1 ml/kg, 15 mg/kg body weight.

The investigator was not aware which formulations were assigned to the codes.

On Day 0, the test compounds were administered topically once with approximately one-fifth of the total volume of drug solution applied to the skin at each of five discrete spots equally placed along the dog's back between the mid-neck and base of the tail. The degree of hair stiffness was graded at 24 and 48 hours after treatment. Blood samples for recovery of plasma were taken from each dog at Day −5, 6, 12, and 24 hours; and 2, 3, 7 and 14 days after treatment. Hair, skin swabs, and skin samples were taken from three sites on each dog at the time of necropsy (Day 14).

All six vehicle control pups had adult *A. caninum* (geometric mean=81.1 worms). Compound of Formula (111) at 15 mg/kg cleared three of six pups of hookworms and reduced hookworm burdens by 97.5% relative to hookworm burdens of the controls ($p<0.05$). Each dosage regimen (10 and 15 mg/kg) of compound of Formula (IV) cleared five of six pups of hookworms and reduced hookworm burdens by 99.4 and 99.8%, respectively, relative to hookworm burdens of the controls ($p<0.05$).

Five of six controls had adult *T. canis* at necropsy (geometric mean=4.4 worms). No ascarids were recovered from any of the treated pups. Efficacy of each of the three topically applied formulations against *T. canis* relative to control was 100% ($p<0.05$).

Example 5

Test of Efficacy of Combination Therapy in Dogs Against Ticks and Fleas

To test the efficacy of the compositions of the invention, spot-on compositions comprising 10% solution of fipronil in combination with either a 5% or 10% solution of the MEM derivative of ivermectin (compound of Formula (III)) were prepared and administered to a group of 6 dogs per study. Efficacy was measured on a weekly basis for infestation of ticks (*Rhipicephalus sanguineus*) and fleas (*Ctenocephalides felis*) and was compared against identical testing using a composition containing 10% fipronil alone.

TABLE 1

Data for efficacy against ticks in dogs

| Composition | Days after treatment | | | | | | |
|---|---|---|---|---|---|---|---|
| | 2 | 9 | 16 | 23 | 30 | 37 | 44 |
| Fipronil 10% (comparative) | 62.1 | 98.9 | 100 | 96.4 | 91.7 | 78.7 | 77.5 |
| Fipronil 10% + MEM derivative 5% | 80.5 | 99.4 | 100 | 100 | 92.8 | 91.7 | 89.8 |
| Fipronil 10% + MEM derivative 10% | 93.0 | 100 | 100 | 100 | 99.3 | 94.4 | 91.1 |

As can be seen from the table, the activity against ticks of the spot-on compositions of the invention show a much greater initial efficacy against ticks (i.e. is faster acting) than fipronil 10% alone. In addition, this improved activity against ticks for the spot-on compositions of the invention is also seen for at least two weeks beyond the 30 day mark.

Figure 2:
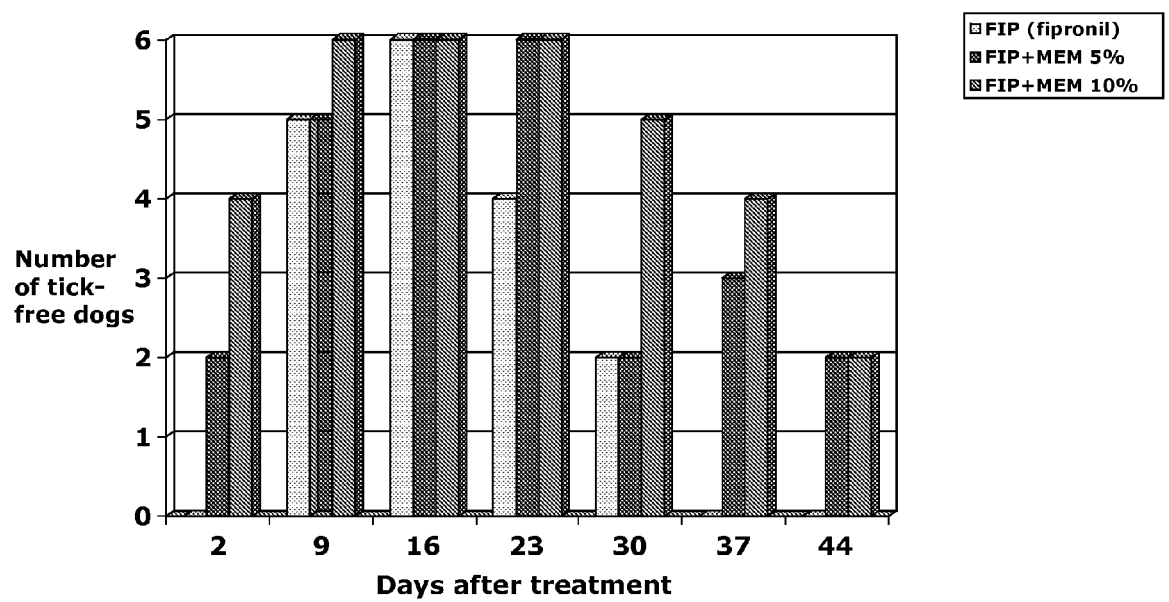
FIG. 2 compares the number of dogs free of fleas after administering a fipronil containing composition vs. a fipronil and ivermectin derivative containing composition.

While there appears to be only marginal differences in efficacy between day 9 through day 30 based only on the observation of the data in Table 1, it is noted that the number of dogs that are completely free of ticks varied greatly in these tests. In FIG. 2, it can be seen that the spot-on compositions of the invention had much improved success in keeping dogs free of ticks relative to composition containing fipronil 10% alone from day 16 through day 44. As such, the compositions of the invention are much more amenable to a once a month administration regimen than a composition containing only fipronil 10%.

Figure 3:
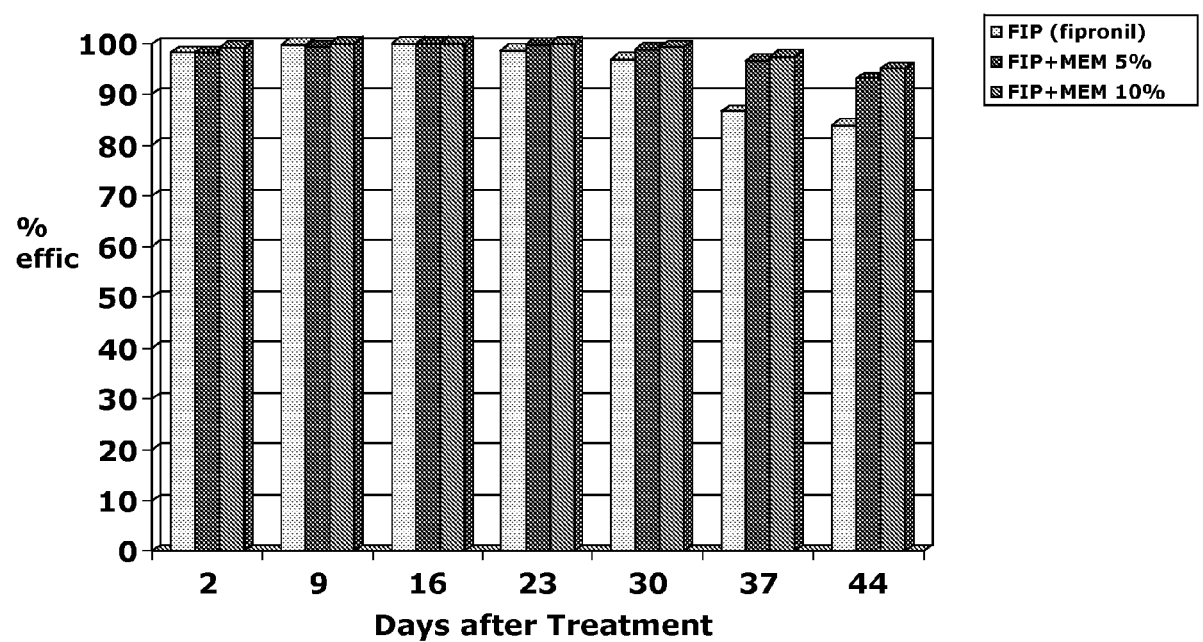
FIG. 3 compares the efficacy against fleas in dogs after administering a fipronil containing composition vs. a fipronil and ivermectin derivative containing composition.
Figure 4:
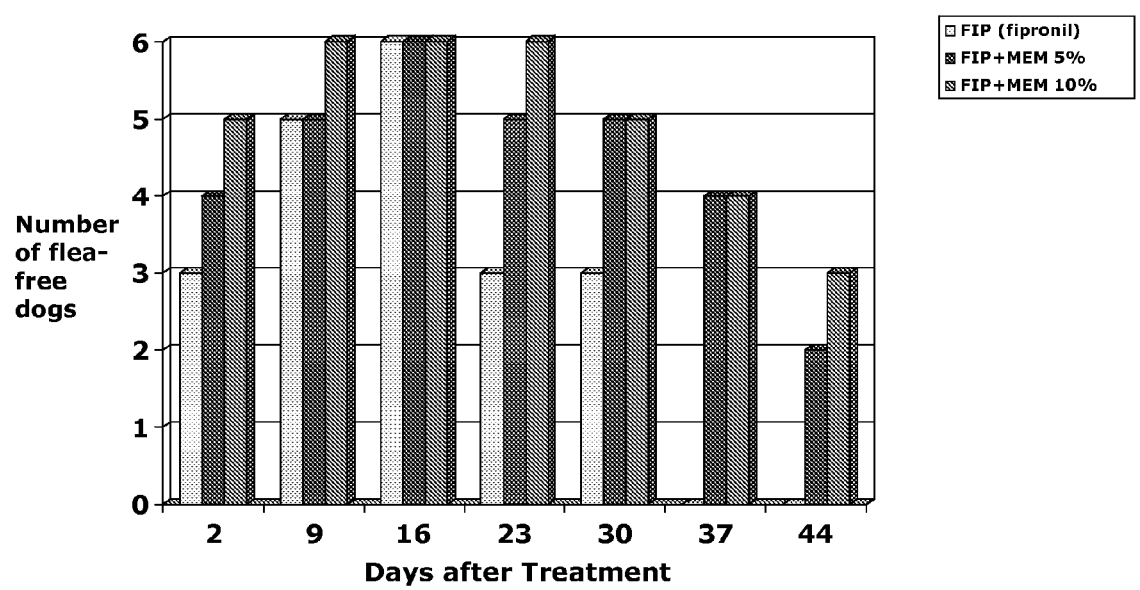
FIG. 4 compares the number of dogs free of fleas after administering a fipronil containing composition vs. a fipronil and ivermectin derivative containing composition.
Figure 5:
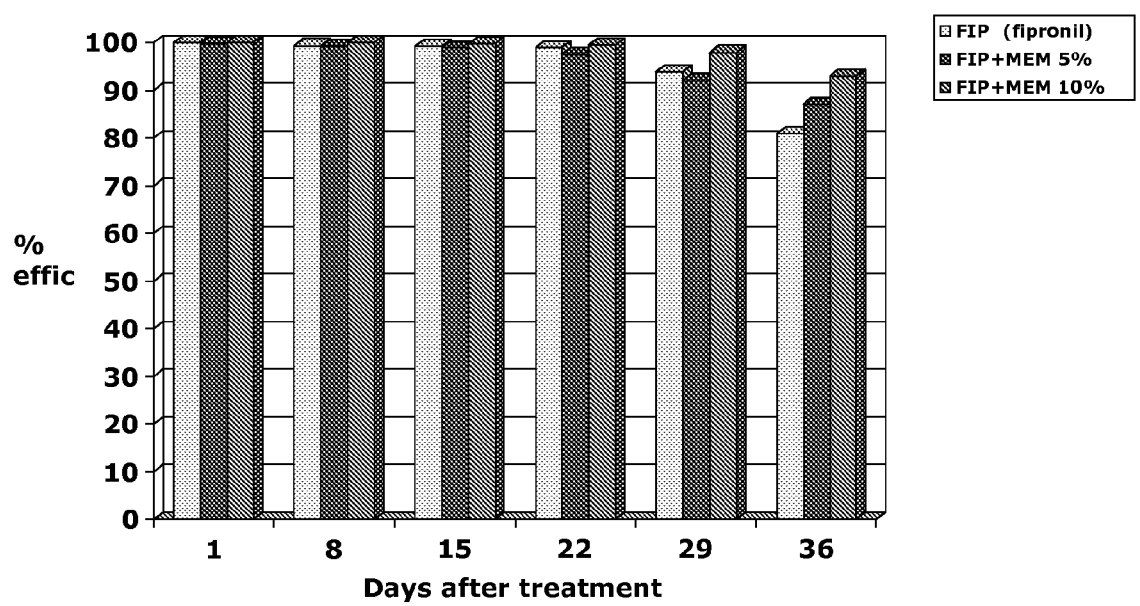
FIG. 5 compares the efficacy against fleas in cats after administering a fipronil containing composition vs. a fipronil and ivermectin derivative containing composition.
Figure 6:
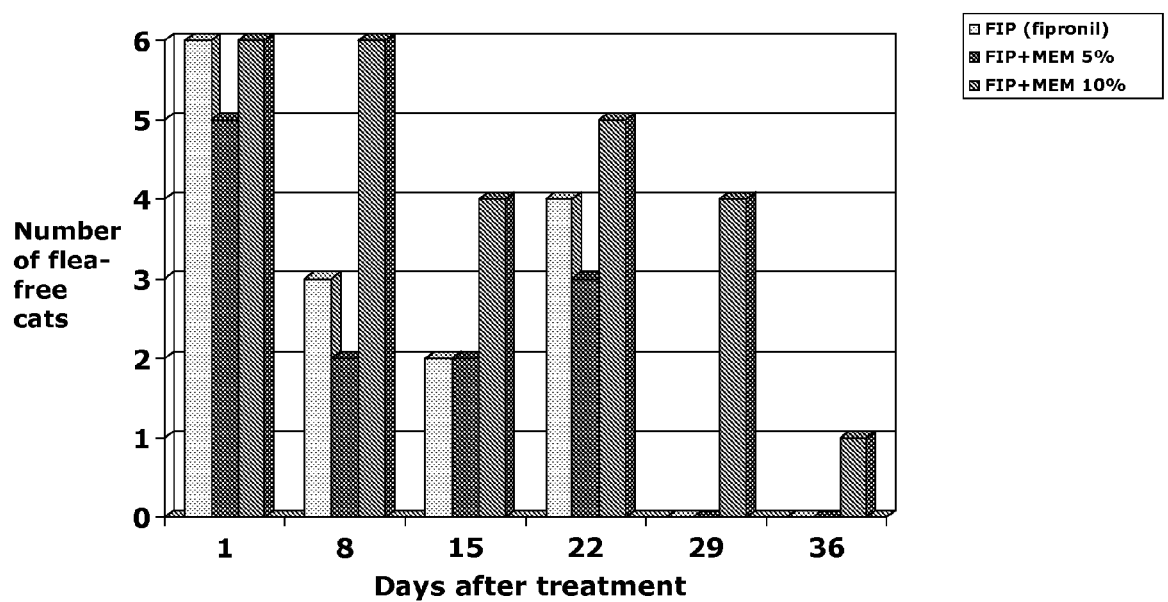
FIG. 6 compares the number of cats free of fleas after administering a fipronil containing composition vs. a fipronil and ivermectin derivative containing composition.

Similarly, although less pronounced that for ticks, the spot-on formulations of the invention showed more efficacy against fleas especially in the time period after the 30 day mark (see FIG. 3) but showed much greater efficacy for maintaining dogs to be completely free of fleas compared to a composition with fipronil 10% alone (see FIG. 4).

Example 6

Test of Efficacy in Cats Against Fleas

To test the efficacy of the compositions of the invention, spot-on compositions comprising 10% solution of fipronil in combination with either a 5% or 10% solution of the MEM derivative of ivermectin (Formula (III)) were prepared and administered to a group of 6 cats per study. Efficacy was measured on a weekly basis for infestation of fleas (*Ctenocephalides felis*) and was compared against identical testing using a composition containing 10% fipronil alone.

TABLE 2

Data for efficacy against fleas in cats

| Composition | Days after treatment | | | | | |
|---|---|---|---|---|---|---|
| | 1 | 8 | 15 | 22 | 29 | 36 |
| Fipronil 10% (comparative) | 100 | 99.3 | 99.1 | 98.9 | 93.9 | 80.9 |
| Fipronil 10% + MEM derivative 5% | 99.7 | 99.1 | 99 | 97.4 | 92 | 87.1 |
| Fipronil 10% + MEM derivative 10% | 100 | 100 | 99.7 | 99.4 | 97.9 | 92.9 |

Similar to the effect seen in dogs, the efficacy against fleas in cats beyond the 30 day mark for the spot-on compositions of the invention are improved over the composition with only fipronil 10%. While there is marginal differences in efficacy prior to the 30 day mark, the spot-on compositions of the invention show vastly improved efficacy in keeping cats completely free of ticks. Measured over 29 days and five measurement dates, the average of the total number of cats which were completely free of fleas when treated with the spot-on compositions of the invention was 5.0 (25 cats/5 measurement dates) whereas the average of the total number of cats which were completely free of fleas when treated with only fipronil 10% was only 3.0 (15 cats/5 measurement dates).

The above description of the invention is intended to be illustrative and not limiting. Various changes or modifications in the embodiments described herein may occur to those skilled in the art. These can be made without departing from the scope and spirit of the invention.

What is claimed is:

1. A compound of the formula (II):

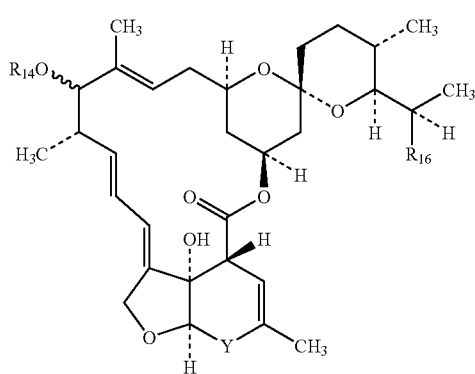

(II)

wherein:
$R_{14}$ represents —$(CH_2)_s$—O—Z
  wherein,
  s is 1 or 2;
Y represents —$CH(OR_{15})$—, —$C(=O)$— or —$C(=NOR_{15})$;
$R_{15}$ represents hydrogen, alkyl or phenyl; and
$R_{16}$ represents —$CH_3$ or —$CH_2CH_3$;
Z is alkenyl, alkynyl, alkanoyloxy, alkoxycarbonyl, alkenoyl, alkynoyl, or aroyl.

2. The compound of claim 1, wherein:
$R_{15}$ represents hydrogen, or $C_1$-$C_8$ alkyl; and
Z is alkenyl or alkynyl.

3. The compound of claim 1, wherein:
$R_{15}$ represents hydrogen, or $C_1$-$C_8$ alkyl; and
Z is alkoxycarbonyl, alkenoyl, alkynoyl, or aroyl.

4. The compound of claim 1, wherein:
$R_{14}$ represents —$(CH_2)_s$—O—Z
  wherein,
  s is 1;
Y represents —$CH(OR_{15})$—;
$R_{15}$ represents hydrogen, or $C_1$-$C_8$ alkyl; and
Z is alkenyl, alkynyl, alkoxycarbonyl or aroyl.

5. The compound of claim 1, which has the formula (IIa) wherein:

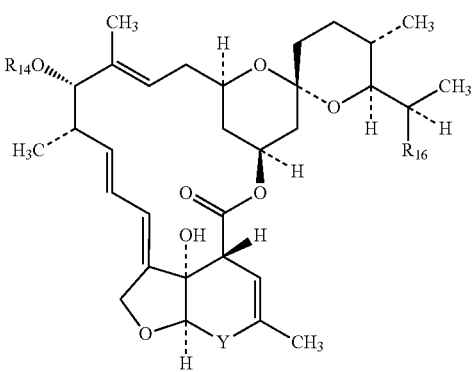

(IIa)

wherein:
$R_{14}$ represents —$(CH_2)_s$—O—Z
  wherein,
  s is 1 or 2;
Y represents —$CH(OR_{15})$—, —$C(=O)$— or —$C(=NOR_{15})$;
$R_{15}$ represents hydrogen, $C_1$-$C_4$ alkyl or phenyl; and
$R_{16}$ represents —$CH_3$ or —$CH_2CH_3$;
Z is alkenyl, alkynyl, alkanoyloxy, alkoxycarbonyl, alkenoyl, alkynoyl, or aroyl.

6. The compound of claim 5 wherein:
$R_{15}$ represents hydrogen, or $C_1$-$C_8$ alkyl; and
Z is alkenyl or alkynyl.

7. The compound of claim 5 wherein:
$R_{15}$ represents hydrogen, or $C_1$-$C_8$ alkyl; and
Z is alkoxycarbonyl, alkenyl, alkynoyl, or aroyl.

8. The compound of claim 5 wherein :
$R_{14}$ represents —$(CH_2)_s$—O—Z
  wherein,
  s is 1;
Y represents —$CH(OR_{15})$;
$R_{15}$ represents hydrogen, or $C_1$-$C_8$ alkyl; and
Z is alkenyl, alkynyl, alkoxycarbonyl or aroyl.

9. The compound of claim 1, which has the formula (IIb):

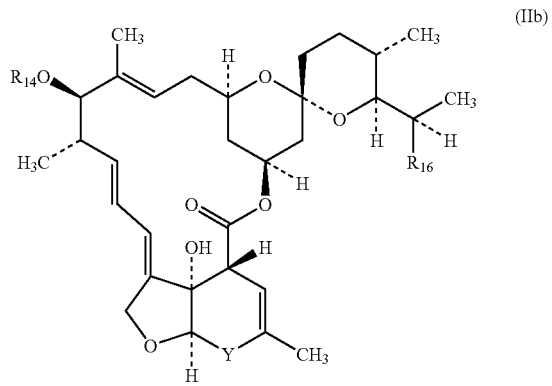

(IIb)

wherein:
$R_{14}$ represents —$(CH_2)_s$—O—Z
  wherein,
  s is 1 or 2;
Y represents —$CH(OR_{15})$—, —$C(=O)$— or —$C(=NOR_{15})$;
$R_{15}$ represents hydrogen, $C_1$-$C_4$ alkyl or phenyl; and
$R_{16}$ represents —$CH_3$ or —$CH_2CH_3$;
Z is alkenyl, alkynyl, alkanoyloxy, alkoxycarbonyl, alkenoyl, alkynoyl, or aroyl.

10. The compound of claim 9 wherein:
Z is alkenyl or alkynyl.

11. The compound of claim 9 wherein:
$R_{15}$ represents hydrogen, or $C_1$-$C_8$ alkyl; and
Z is alkoxycarbonyl, alkenoyl, alkynoyl, or aroyl.

12. The compound of claim 9, wherein:
wherein:
$R_{14}$ represents —$(CH_2)_s$—O—Z
  wherein,
  s is 1;
Y represents —$CH(OR_{15})$;
$R_{15}$ represents hydrogen, or $C_1$-$C_8$ alkyl; and
Z is alkenyl, alkynyl, alkoxycarbonyl or aroyl.

13. A composition for the treatment of a parasite infestation in birds or mammals which comprises a pharmaceutically effective amount a compound of formula (II):

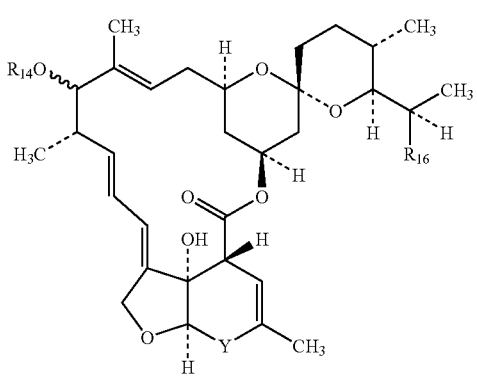

(II)

wherein:
$R_{14}$ represents —$(CH_2)_s$—O—Z
 wherein,
 s is 1 or 2;
Y represents —$CH(OR_{15})$—, —$C(=O)$— or —$C(=NOR_{15})$;
$R_{15}$ represents hydrogen, alkyl or phenyl;
$R_{16}$ represents —$CH_3$ or —$CH_2CH_3$; and
Z is alkenyl, alkynyl, alkanoyloxy, alkoxycarbonyl, alkenoyl, alkynoyl, or aroyl;
a pharmaceutically effective amount of at least one compound of the formula (I)

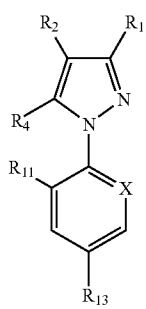

(I)

wherein:
$R_1$ is a halogen, CN or alkyl;
$R_2$ is $S(O)_nR_3$, 4,5-dicyanoimidazol-2-yl or haloalkyl;
$R_3$ is alkyl or haloalkyl;
$R_4$ represents a hydrogen, halogen, $NR_5R_6$, $S(O)_mR_7$, $C(O)R_7$, $C(O)OR_7$, alkyl, haloalkyl, $OR_8$ radical or —N=C($R_9$)($R_{10}$) radical;
$R_5$ and $R_6$ independently represent hydrogen, alkyl, haloalkyl, C(O)alkyl, $S(O)_rCF_3$, alkoxycarbonyl; or
$R_5$ and $R_6$ can together form a divalent alkylene radical which is optionally interrupted by one or two divalent heteroatoms;
$R_7$ represents an alkyl or haloalkyl;
$R_8$ represents an alkyl, haloalkyl or hydrogen;
$R_9$ represents an alkyl or hydrogen;
$R_{10}$ represents an optionally substituted aryl or an optionally substituted heteroaryl group;
$R_{11}$ and $R_{12}$ represent, independently of one another, hydrogen, halogen, CN or $NO_2$;
$R_{13}$ represents a halogen, haloalkyl, haloalkoxy, $S(O)_qCF_3$ or $SF_5$;
m, n, q and r represent, independently of one another, an integer equal to 0, 1 or 2;

X represents a trivalent nitrogen atom or a C—$R_{12}$ radical, the three other valencies of the carbon atom forming part of the aromatic ring; and
a pharmaceutically acceptable carrier.

14. The composition of claim 13, wherein in formula (II):
Y represents —$CH(OR_{15})$—;
$R_{15}$ represents hydrogen, or $C_1$-$C_8$ alkyl; and
Z is alkenyl, alkanoyloxy, alkoxycarbonyl or aroyl.

15. The composition of claim 13, wherein in formula (I):
$R_1$ is CN or $C_1$-$C_4$ alkyl;
$R_2$ is $S(O)_nR_3$;
$R_3$ is $C_1$-$C_4$ alkyl or $C_1$-$C_4$ haloalkyl;
$R_4$ represents $NR_5R_6$, $C_1$-$C_4$ alkyl, $C_1$-$C_4$ haloalkyl, $OR_8$ radical;
$R_5$ and $R_6$ independently represent hydrogen, $C_1$-$C_4$ alkyl, or C(O)alkyl;
$R_7$ represents $C_1$-$C_4$ alkyl or $C_1$-$C_4$ haloalkyl;
$R_8$ represents $C_1$-$C_4$ alkyl, $C_1$-$C_4$ haloalkyl or hydrogen;
$R_{11}$ and $R_{12}$ represent, independently of one another, hydrogen, or halogen;
$R_{13}$ represents a halogen, $C_1$-$C_4$ haloalkyl, $C_1$-$C_4$ haloalkoxy, or $SF_5$; and
m, n, q and r represent, independently of one another, an integer equal to 0, 1 or 2.

16. The composition of claim 13, wherein in formula (I):
$R_1$ is CN;
$R_2$ is $S(O)_nR_3$;
$R_3$ is $CF_3$;
$R_4$ represents $NR_5R_6$;
$R_5$ and $R_6$ independently represent hydrogen;
$R_{11}$ and $R_{12}$ represent Cl;
$R_{13}$ represents $CF_3$;
n is 1; and
X represents C—$R_{12}$;
and wherein in formula (II):
Y represents —$CH(OR_{15})$—;
$R_{15}$ represents hydrogen, or $C_1$-$C_8$ alkyl; and
Z is, alkanoyloxy or alkoxycarbonyl.

17. A spot-on or pour-on composition for the treatment of a parasite infestation in birds or mammals which comprises a pharmaceutically effective amount of the compound of formula (III):

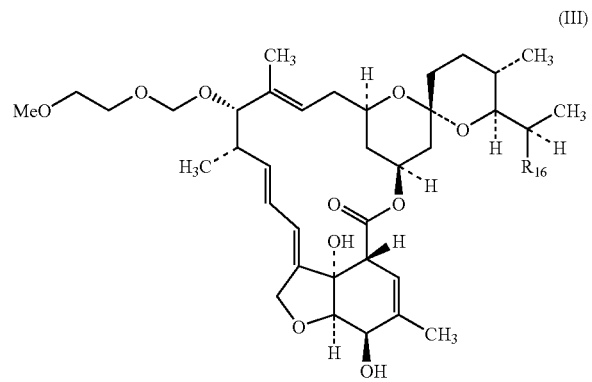

(III)

wherein $R_{16}$ represents —$CH_3$ or —$CH_2CH_3$;
a pharmaceutically effective amount of at least one compound of the formula (I):

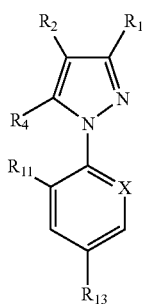

wherein:
$R_1$ is CN;
$R_2$ is $S(O)_n R_3$;
$R_3$ is $CF_3$;
$R_4$ represents $NR_5 R_6$;
$R_5$ and $R_6$ independently represent hydrogen;
$R_{11}$ and $R_{12}$ represent Cl;
$R_{13}$ represents $CF_3$;

n is 1; and
X represents C—$R_{12}$; and
a pharmaceutically acceptable liquid carrier.

18. The composition of claim 13 or 17, which further comprises at least one additional macrocyclic lactone compound.

19. The composition of claim 18, which further comprises a cestodal agent.

20. The composition of claim 19, wherein the one additional macrocyclic lactone compound is eprinomectin and the cestodal agent is praziquantel.

21. The composition of claim 13, which further comprises a nitroguanidine or pyridylmethylamine insecticide.

22. The composition of claim 21, wherein the nitroguanidine or pyridylmethylamine insecticide is imidacloprid.

23. A method for the treatment of a parasitic infestation in a bird or mammal which comprises administering a pharmaceutically effective amount of the composition of claim 13 or 17.

24. The method of claim 23, wherein the mammal is a dog or cat.

* * * * *